United States Patent [19]

Hudson et al.

[11] 4,304,715

[45] Dec. 8, 1981

[54] ENKEPHALIN ANALOGUES

[76] Inventors: Derek Hudson, 23A Elm Rd., Wembley, Middlesex; Robert Sharpe, 99 King House, Ducane Rd., London, W12; Michael Szelke, 10 North Dr., Ruislip, Middlesex, all of England

[21] Appl. No.: 112,122

[22] Filed: Jan. 14, 1980

Related U.S. Application Data

[63] Continuation-in-part of Ser. No. 923,478, Jul. 10, 1978, Pat. No. 4,198,398.

[30] Foreign Application Priority Data

Jun. 8, 1979 [GB] United Kingdom ............... 20124/79

[51] Int. Cl.$^3$ ........................................... C07C 103/52
[52] U.S. Cl. ............................................. 260/112.5 R
[58] Field of Search ................................. 260/112.5 R

[56] References Cited

U.S. PATENT DOCUMENTS 4,028,319  6/1977  Jones, Jr. et al. ............ 260/112.5 R
4,198,398  4/1980  Hudson et al. ............... 260/112.5 R

OTHER PUBLICATIONS

Biological Abstract, 1978, pp. 41745, vol. 66.

Primary Examiner—Delbert R. Phillips
Attorney, Agent, or Firm—Larson and Taylor

[57] ABSTRACT

Compounds corresponding in structure to enkephalin or polypeptide analogues thereof, wherein one or more peptide links of the enkephalin or analogue is represented by a group or groups the same or different selected from dimethylene, hydroxydimethylene, methylene-imino and ketomethylene groups and/or wherein adjacent peptide bond nitrogen atoms are linked by a carbonyl or thiocarbonyl group.

21 Claims, No Drawings

ENKEPHALIN ANALOGUES

RELATION TO OTHER APPLICATIONS

This application is a continuation-in-part of our application Ser. No. 923,478 filed July 10, 1978, now Pat. No. 4,198,398.

BACKGROUND

The invention relates to enkephalin analogues or, as they are also referred to herein, isosteres.

Enkephalin, specifically methionine enkephalin, is the pentapeptide

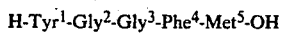

H-Tyr$^1$-Gly$^2$-Gly$^3$-Phe$^4$-Met$^5$-OH

Since its discovery a great deal of work has been done synthesising analogues with a view to elucidation of the mechanism of action of enkephalin itself and clinical use of the analogues.

The past decade has witnessed an unprecedented growth of knowledge in the field of biologically active peptides. The discovery of a new naturally occurring peptide is usually followed by the synthesis of analogues in order to obtain more potent, more selective or longer acting compounds, or antagonists of the parent peptide. Since peptides are synthesized by linking successive amino acids, it is technically easy and therefore tempting to synthesize analogues in which some of the native amino acid residues are replaced by others, sometimes of the unnatural D-configuration. The structure-activity correlations derived in this way reflect the contribution of individual amino acid residues.

We have essentially taken a different approach, and set out to investigate the role the backbone plays in the biological properties of peptides. This backbone, consisting of the monotonous polymer

is common to all peptides. Attached to it at the α-carbon atoms are the amino acid side-chains, and it is the sequence and variety of these that endow the peptide with its peculiar physical, chemical and biological properties. In practical terms, our broad aim has been to synthesize isosteric analogues, in which the amino acid side-chains of the parent peptide are retained but parts of the peptide backbone are replaced with other, stereochemically similar residues.

Since the metabolic instability of peptides resides in the backbone, isosteric substitutions that are resistant to proteolysis may endow the analogue with increased stability and a prolonged duration of action provided, of course, that they are replacing susceptible parts of the backbone. The variations we propose are fully set out below, but for example reduced analogues, obtained by chemical reduction of the amide carbonyl to methylene, introduce a basic centre into the backbone and slightly alter the orientation of the side-chains. Hydrocarbon analogues, in which the peptide bond —CO—NH— is replaced by —CH$_2$—CH$_2$— show a stereochemically very slight change, but the backbone is more lipophilic and is incapable of forming a hydrogen bond at the site of replacement.

THE INVENTION

The invention essentially provides compounds corresponding in structure to enkephalin or polypeptide analogues thereof, wherein one or more of the peptide groups —CO—NH— of the backbone are replaced by a group or groups, the same or different, selected from dimethylene —CH$_2$—CH$_2$—, hydroxydimethylene —CH(OH)—CH$_2$— or —CH(OR)—CH$_2$—, methylene-imino

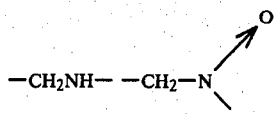

or —CH$_2$—NR— (R is in either case an aliphatic or other protective group as below), and ketomethylene —CO—CH$_2$—, or any simple chemical modifications of these, and/or any adjacent pair of peptide-bond nitrogen atoms of the backbone

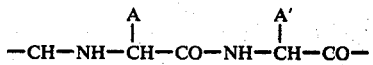

(where A and A' are the side chains of adjacent amino acid residues), is linked to form the structure

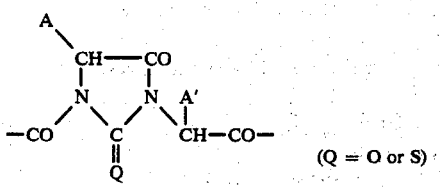

(Q = O or S)

that is to say a carbonyl or thiocarbonyl group links the nitrogen atoms of the residues, as in a hydantoin.

It will be understood that the side chains A and A' will be selected preferably from those of the natural amino acids or the corresponding D-acids and will in the case that the acid is glycine be merely a hydrogen atom, but it is within the spirit and scope of the invention as herein claimed to use protected or otherwise modified side chains where such do not deleteriously affect the biological properties of the compounds.

The usual natural amino acids, with the side chains marked off from the backbone-forming —CH(NH$_2$)COOH unit, are:

Glycine
H—CH(NH$_2$)COOH
Alanine
CH$_3$—CH(NH$_2$)COOH
Valine
(CH$_3$)$_2$CH—CH(NH$_2$)COOH
Leucine
(CH$_3$)$_2$CHCH$_2$—CH(NH$_2$)COOH
Isoleucine
CH$_3$CH$_2$CH(CH$_3$)—CH(NH$_2$)COOH
Phenylalanine

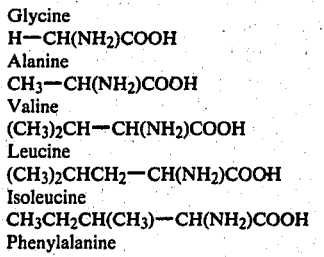

Tyrosine

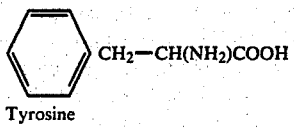

-continued

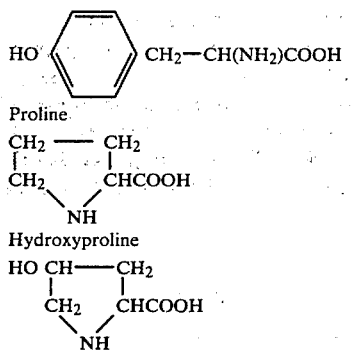
Proline
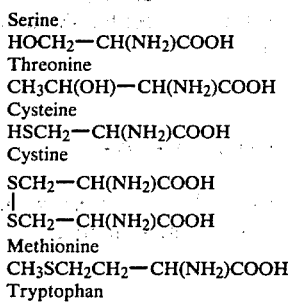
Hydroxyproline
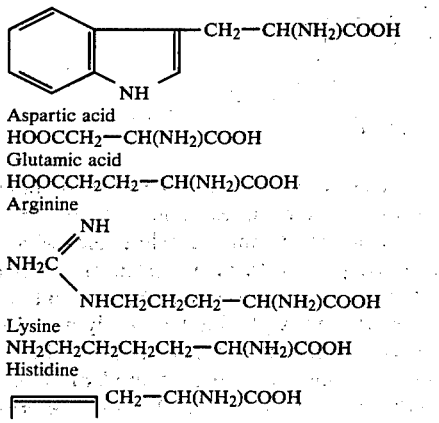

(In peptides containing proline and hydroxyproline the side chains are thus linked to the backbone at the peptide nitrogen as well as the α-carbon)

Serine
HOCH₂—CH(NH₂)COOH
Threonine
CH₃CH(OH)—CH(NH₂)COOH
Cysteine
HSCH₂—CH(NH₂)COOH
Cystine
SCH₂—CH(NH₂)COOH
|
SCH₂—CH(NH₂)COOH
Methionine
CH₃SCH₂CH₂—CH(NH₂)COOH
Tryptophan $$\text{[indole]}-CH_2-CH(NH_2)COOH$$

Aspartic acid
HOOCCH₂—CH(NH₂)COOH
Glutamic acid
HOOCCH₂CH₂—CH(NH₂)COOH
Arginine $$\underset{NH_2C}{\overset{NH}{\diagdown}}-NHCH_2CH_2CH_2-CH(NH_2)COOH$$

Lysine
NH₂CH₂CH₂CH₂CH₂—CH(NH₂)COOH
Histidine $$\text{[imidazole]}-CH_2-CH(NH_2)COOH$$

Preferred conbinations for A and A' are (i) A as the side chain of Gly, aza-Gly, aza-Ala or any D-amino acid residue particularly D-Ala, D-Thr, D-Ser or D-Met, and A' as the side chain of Gly.

(ii) A as the side chain of Gly and A' as the side chain of Phe, N-substituted (particularly N-methyl)-Phe or dehydro-Phe all optionally substituted in the ring by hydroxy, halo, nitro or other groups, or alternatively cyclohexylalanine.

(iii) A as the side chain of Phe, N-substituted (particularly N-methyl) -Phe or dehydro-Phe all optionally substituted in the ring by hydroxy, halo, nitro or other groups, or alternatively cyclohexylalanine, and A' as any D- or L-amino acid residue particularly Leu, Nle, Met or the sulphoxide of Met all as such or in aza form; Pro or Hypro; or homoserine lactone; or formal derivatives of any of these in which the terminal

group is replaced by —CH₂—Z (Z is —NH₂, —NHR, —N(R)₂, —OH or —OR where R is an aliphatic or other protective group as below) or by hydrogen.

It will be understood that the amino-terminal residue of the compounds, tyrosine in the case of enkephalin itself, should not be involved in linking as above unless there is further modification to provide, still, a positively charged terminal corresponding to that given by the tyrosine.

A general formula for the compounds is for example:

R-Tyr-X-Gly-B-Y-Z where (a) the peptide bond between one or more of the residues Tyr, X, Gly, B and Y is replaced as above, optionally further with the nitrogen of one or more of the remaining peptide groups carrying a protective aliphatic or other group as

 (R being as below)

and (b) R is an aliphatic or other protective group including methyl, ethyl, propyl, cyclopropyl, cyclopropylmethyl, butyl, allyl, phenyl, benzyl or the like or simple halogenated (in particular fluorinated) derivatives of the same or, more important, formyl, acetyl, or other acyl groups or simple halo-substituted derivatives thereof such as chloroacetyl or trifluoroacetyl, or a substituted derivative such as

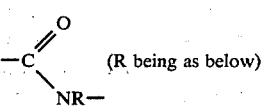

where R¹ may be methyl, ethyl, propyl, cyclopropyl, cyclopropylmethyl, butyl, allyl or the like, or phenyl or benzyl or ring substituted phenyl or benzyl derivatives, tertiary butyl, or substituted derivatives such as phenylisopropyl, diphenylisopropyl or fluorenylmethylene, or any simple chemical modification of any of these.

and (c) Z is NH₂, NHR, N(R)₂, OH or OR, where R is as above, and (d) —X is Gly, aza-Gly, aza-Ala or any D-amino acid residue particularly D-Ala D-Thr D-Ser or D-Met —B is Phe, N-substituted (particularly N-methyl) —Phe or dehydro-Phe all optionally substituted in the ring by hydroxy, halogen, nitro or other groups, or alternatively cyclohexylalanine —Y is any D- or L-amino acid residue particularly Leu, Nle, Met (the most preferred), or the sulphoxide of Met all as such or in aza form; Pro or Hypro; or homoserine lactone; or formal derivatives of any of these in which the terminal

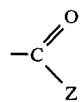

group is replaced by —CH₂—Z or hydrogen

The compounds in which the residue Y has a terminal amide group are generally more useful, being resistant to natural carboxypeptidases. For the same reason the D-acids are preferred to the L-acids.

The various analogues (isosteres) are from time to time respectively referred to herein as hydrocarbon —CH₂—CH₂—, hydroxy —CH(OH)—CH₂—

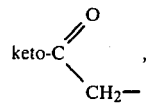

reduced —CH₂—NH— and cyclised isosteres.

It will be understood that any of the compounds may be in salt form or protected at amino or other groups in ways not specifically set out above and that bare reference to a compound in the description or claims covers the compound in any such form.

It will further be understood throughout the above that while compounds containing five amino acid or like residues, the same number as enkephalin itself, are primarily in mind, further residues, for example one or two, may be present and compounds containing them are within the spirit and scope of the invention as defined in the claims hereof. To retain the biological activity of the compounds such further residues should be at the amino or carboxyl terminal, and not interrupt the portion of the structure that corresponds to enkephalin. If present at the amino terminal the further residue should be such as to retain a positive charge, or the capability of it at physiological pH's, and should thus be lysine or arginine or a residue with a free amino (—NH₂) group.

General Discussion of Syntheses

An example is included of a general method of synthesis of keto and hydroxy analogues and hydrocarbon analogues derived from them, and also an alternative and synthesis of Tyr-Gly hydrocarbon analogues by repeated Ardnt Eistert reaction.

Reduced isosteres (i.e. methylene imino) may be synthesised by a variety of routes including reduction (Examples 3 and 4, H215 and H216) but also by substitution as with Examples 6 to 8, H218–220, and details of the synthesis of these last examples are included.

The general method for preparation of keto and hydrocarbon isosteres is given schematically below and then discussed briefly:

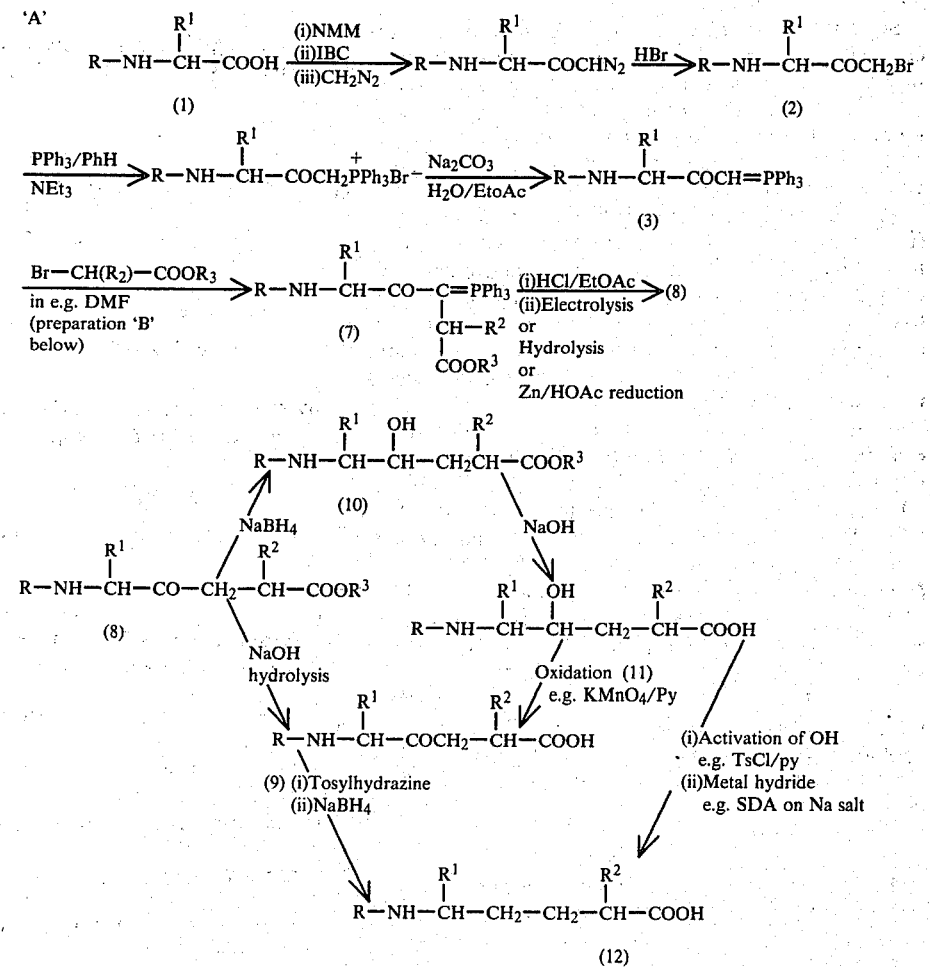

-continued
Summary scheme

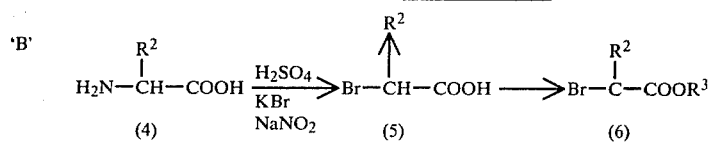

Key
R = Any suitable N-protecting group e.g. t-butoxycarbonyl
DMF = dimethylformamide
NMM = N-methylmorpholine
IBC = isobutylchloroformate
TsCl/py = tosyl chloride in pyridine
SDA = sodium dihydro-bis(2-methoxyethoxy) aluminate Thus for Gly-Phe isosteres:
$R^1 = H$ $R^2 = CH_2C_6H_5$ and for Gly-Gly isosteres (as in Example 5, H222)
$R^1 = R^2 = H$ Thus amino acid (1) protected at the N-terminal and if necessary in the side chain $R^1$ is first converted into its diazoketone by treatment with N-methylmorpholine, isobutylchloroformate and diazomethane. An alternative is simply to treat the acid chloride with diazomethane. Then the diazoketone is treated with hydrogen bromide in ethyl acetate to give the α-bromoketone (2). This ketone is then treated with triphenyl phosphine in the presence of triethylamine, giving the α-ketophosphonium salt which in turn is converted to the ylid (3) by treatment with sodium carbonate.

Separately, the amino acid (4) which is to form the carboxyl terminal of the isostere, with its side chain $R^2$ protected if necessary, is converted to the corresponding α-bromo acid (5) by treatment with sulphuric acid, potassium bromide and sodium nitrite, and the bromo acid is then converted to its ester (6), e.g. by treatment with a diazo alkane.

The ylid (3) is then alkylated by reaction with ester (6) in a solvent such as dimethylformamide to give a new ylid (7), from which the triphenyl phosphine moiety is removed in per se known manner by electrolysis, hydrolysis, or zinc/acetic acid reduction. The product is an ester (8) of the keto-isostere, which can be converted to the free N-(and side chain) protected keto-isostere acid (9) by hydrolysis.

Alternatively the ester can be selectively reduced, for example with sodium borohydride, to the corresponding hydroxy compound (10). This hydroxy compound, after hydrolysis, can be re-oxidised to the keto-isostere if required, for example by alkaline potassium permanganate, or it can be converted to the N-(and side chain) protected hydrocarbon isostere (12) by activation of the hydroxyl group with tosyl chloride in pyridine and its subsequent removal with a metal hydride such as sodium dihydro-bis(2-methoxyethoxy) aluminate.

A further and preferred route to the hydrocarbon isostere is from the keto-isostere ester (8) via the keto-isostere itself, by direct reaction of the keto-isostere with tosylhydrazine followed by reduction with sodium borohydride.

Particular Compounds

Among 'hydrocarbon' isosteres a particular compounds, both representing replacement of a peptide link by dimethylene, is:

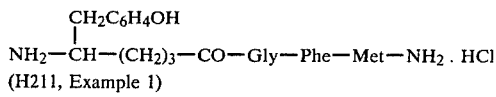
(H211, Example 1)

in which the Tyr-Gly residues of enkephalin are replaced by the residue:

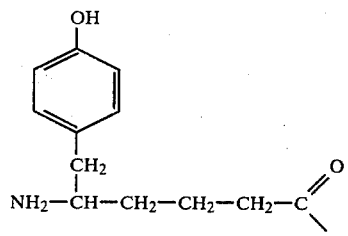

The acid giving this residue is available from protected derivatives of tyrosine, for example:

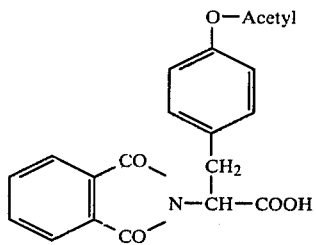

by repeated application of the Arndt-Eistert reaction.
Further particular compounds are:

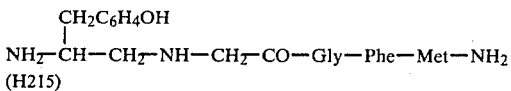
(H215)

and the corresponding methioninol ('Metol') compound (H216) (Examples 3 and 4) representing replacement of Tyr-Gly peptide link by a methylene-imino group, and:

and the corresponding Metol compound (H219) and Met-NH2 compound (H220) (Examples 6, 7 and 8), representing a similar replacement but of the Gly-Gly peptide link.

Still another particular compound (Example 5) is:

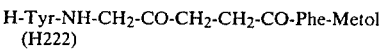
(H222)

representing replacement of Gly-Gly peptide link by a ketomethylene group.

Compounds within the above general formula where a peptide group is represented by —$CH_2$—NR— are H224, H226, H228 and H232 in Examples 9, 11, 14 and 16 respectively, R being benzyloxycarbonyl. Other groups may be attached similarly. The cyclised compounds are represented by H229 (Example 13) H230 (Example 15) and H238 (Example 20). Compounds where a peptide group is replaced by —CH(OH)—$CH_2$ or derivatives thereof may be made following reaction scheme "A" set out earlier but directed to compounds such as (10) or (11) in that scheme for example generally following the procedure of Example 13 below to give the the compound H-Tyr-NHCH$_2$CH(OH)-CH$_2$CH$_2$CO-Phe-MetOH where the Gly$^2$-Gly$^3$ peptide bond if enkephalin is represented by

—CH(OH)—$CH_2$—

Where derivatives are required the hydroxy group of compounds such as (10) may for example be selectively alkylated with an alkyl halide such as methyl iodide and a base such as potassium carbonate or silver oxide, and the carboxyl protecting group R$^3$ removed by hydrolysis.

Compounds according to the general formula with variations in —X— and —B— are available by the synthetic methods given herein where for example substituted Phe groups may be incorporated by the methods given for Phe itself in the specific compounds of the Examples. For variation at —Y— the method exemplified in the preparation of compound H232 herein (Example 16) Y is methioninol (abbreviated Metol), is general.

The invention extends to the following specific compounds (1) H—Tyr—DAla—Gly—NHCHCH$_2$—NHCHCH$_2$OH
                                     |             |
                                     CH$_2$Ph   CH$_2$CH$_2$SCH$_3$ H225 (Example 10)

(2) the corresponding Gly$^2$ compound H227 (Example 12) and (3) H—Tyr—DAla—NHCH$_2$CH$_2$—Phe—NHCHCH$_2$OH
                                                              |
                                                              CH$_2$CH$_2$SCH$_3$ H231 (Example 17)

and to all the other compounds of the general formula R-Tyr-X-Gly-B-Y-Z that are specifically set out herein and are not claimed in Ser. No. 923 478.

Activity

Significant brain radio receptor assay activity is shown by the analogues, and numerical results are given herein. Activity is also shown in the guineapig ileum system, which is known to correlate with human analgesic properties, and in the mouse vas deferens system.

Among the test results referred to, with Met-Enkephalin for comparison, are:

| Analogue | Activity Relative to Met Enkephalin | | |
|---|---|---|---|
| | G.P.I. | M.V.D. | R.R.A. |
| H211 (Example 1) | | | |
| Tyr$^1$—Gly$^2$ hydrocarbon isotere Enk-NH$_2$ H215 (Example 3) | 3% | 0.9% | 9% |
| Tyr$^1$—Gly$^2$ reduced isotere-Enk NH$_2$ H216 (Example 4) | 56% | N.D. | 50% |
| Tyr$^1$Gly$^2$ reduced isotere-Enkol H218 (Example 6) | 83% | N.D. | 200% |
| Gly$^2$—Gly$^3$ reduced isotere-Enk H219 (Example 7) | 1% | N.D. | 5% |
| Gly$^2$—Gly$^3$ reduced isotere-Enkol H220 (Example 8) | 0.3% | N.D. | 3% |
| Gly$^2$—Gly$^3$ reduced isotere-Enk-NH$_2$ (Comparison) | 0.3% | N.D. | 3% |
| Met Enkephalin | 100% | 100% | 100% |

Notes
(i) G.P.I. stands for guinea pig ileum
(ii) M.V.D. stands for mouse vas deferens
These assays which are opiate assays measuring inhibition by the test compound of electrically induced contractions of isolated preparations were performed as described in the literature
Hughes J., Kosterlitz, H. W. & Leslie, F. M. Br. J. Pharmac, 53, 371–381, 1968
Kosterlitz, H. W., and Watt, A. J., Br. J. Pharmac. Chemother., 33, 266–276 (1968)
(iii) R.R.A. stands for radio receptor assay; based on the concentration required to displace 50% of titrated naloxone from rat brain membranes. The displacements were carried out against ($^3$H)-naloxone (1nM) in 0.1 M sodium chloride/50nM Tris buffer at pH 7.4; incubations were for 15 minutes in the presence of bacitracin. For general reference to the method see literature as discussed in "Opiate Receptor Mechanisms", S. H. Snyder and S. Matthysse eds, MIT Press, 1975, for details see below.

We further have indications that the analogues stimulate release of prolactin and growth hormone from the pituitary. Reference to release by certain known enkephalin analogues is given in L. Cusan, A. Dupont, G. S. Kledzik, F. Labrie, D. H. Coy, A. Schally, Nature 268, 544 (1977).

Also, we have indications of in vivo analgesic effects of the analogues. The compound H211 cause analgesia lasting for several minutes when administered intraventricularly to rats, as determined by the tail flick assay (Ref. D'Amour, F. E. Smith, D. L., J. Pharm. 72, 74–79 (1941).)

Besides these results we have favourable indications of a considerable range of activities, in some of which a relatively low activity in the above brain membrane displacement or guinea pig ileum tests in an advantage in that other activities can be made use of without excessive opiate effect. The activities as a whole are:

| | |
|---|---|
| CNS (Central Nervous System) Activity | Analgesic, anaesthetic, sedative, hypnotic, psychotropic and behavioural effects, particularly the first and last of these |
| Neuro-Endocrine Activity | Affecting the release of hormones from the pituitary gland in particular GH (growth hormone) and prolactin |
| Peripheral Effects | Interaction with intestinal or other peripheral receptors, e.g. in suppression of diarrhoea |

Broadly the invention gives the potential compared with enkephalin itself of increased stability in the body, with therefore a prolonged duration of effect and possible intranasal and/or oral administration, and of variations in properties giving increased selectivity or potency and improved pharmaco-kinetics and/or pharmacodynamics.

EXAMPLES AND DETAILS OF ASSAY

In the Examples the synthesis of a number of further specific compounds is given, those of Examples 9 to 17 being summarised in the table accompanying this specification as Appendix I. The table sets out the relation of the compounds to Met$^5$-enkephalin and gives their activity in the test of Bradbury et al described below.

The final Examples 18 to 21 (compounds H236 to H239) are represented in the table accompanying the specification as Appendix II.

It will be noted that H236 is a 'hydroxy' isostere. Other valuable compounds are those with the Tyr$^1$-Gly$^2$ peptide bond replaced by a hydroxy isostere, which may be synthesized by the methods disclosed herein.

Activity Test, Details

R.R.A. The following test is essentially that of Bradbury et al, Nature 260 293-295 (1976), an opiate binding assay, and is referred to in Examples 9 to 17 and Table I.

A hypotonically lysed (10 mM Tris-HCl, pH 7.4), extensively washed crude synaptosome preparation was made from whole supratentorial rat brain. The membranes were incubated with the peptides in 0.05 M Tris-HCl buffer pH 7.6 with 0.1 M NaCl, 0.1% bovine serum albumin and 0.1% bacitracin containing tritiated naloxone (New England Nuclear, 20 Ci mmole$^{-1}$, $1 \times 10^{-9}$ M). After 20 minutes incubation at 25° the suspension was centrifuged (15,000 g, 1.5 minutes), the pellets rapidly and superficially washed with 0.1 m NaCl in 0.05 M Tris-HCl buffer pH 7.6, the pellets resuspended in water (0.5 ml) and solubilised with scintillator (6 g/liter of PPO in toluene containing 20% (v/v) Triton X 100), counted at 30% efficiency to determine the bound counts. Specific binding was defined as that fraction of the bound radioactivity displaced by morphine ($10^{-5}$ M). Incubations were carried out in triplicate, in at least two separate experiments. Standards of naloxone, Met$^5$-enkephalin and Nle$^5$-enkephalin were used.

Activity in the above test procedure is pharmacologically significant whether higher or lower than naturally occurring Met$^5$-enkephalin. The structure of the compounds of the invention renders them more resistant than enkephalin itself to enzymic degradation in the body and therefore of longer lasting effect. Natural enkephalin is very highly potent, and thus weaker as well as stronger effects are of value.

In relation to the structures it will be noted for example that in H224-H227 the Phe$^4$-Met$^5$ peptide bond is replaced by a methylene-imino isostere, whereas in H228 the Gly$^3$-Phe$^4$ peptide bond is altered in the same way. The relation of all the compounds to Met$^5$-Enkephalin is shown in the tables. All the compounds exhibit significant levels of activity, three of them being more potent than Met$^5$-enkephalin used as a standard. (Nle$^5$-enkephalin with which compound H228 was compared is itself more active in this test system than Met$^5$-enkephalin, the natural material.)

Detailed syntheses—Enkephalin (Comparison and general information)

Solid phase peptide synthesis is the preferred method. A 1.4% crosslinked 100-200 mesh resin prepared by copolymerisation of acetoxystyrene (10 mole %), styrene and divinylbenzene is for example suitable, after deacetylation.

The following description is of a preparation by successive reaction cycles of enkephalin itself, illustrating steps useful in the preparation of the analogues of the invention. The phenolic resin was generated by overnight treatment of the acetoxy resin with excess hydrazine hydrate in a mixture of dioxan and dimethylformamide (DMF). Each synthetic operation was separated and followed by thorough washing with dichloromethane, propan-2-ol and again dichloromethane to swell, shrink and then reswell the resin. In the coupling step of the first cycle BOC-methionine (3 equivalents) was added to the resin using dicyclohexylcarbodiimide (DCCI) in the presence of pyridine (giving a substitution of 0.4 m mole/g after 3 hours reaction). Unreacted phenolic-hydroxyl groups were blocked by two acetylation steps using acetic anhydride-triethylamine in DMF. Acid deprotection was accomplished with 50% trifluoroacetic acid in dichloromethane containing 2% diethyl phosphite and 2%, 1,2-ethanedithiol (1 min prewash, then 15 minutes and this process repeated after washing). The methionine phenyl ester resin trifluoroacetate salt was exchanged, using 0.075 M hydrogen chloride in DMF, to the hydrochloride salt. In the coupling step of the second cycle a mixture of BOC-phenylalanine (4 equivalents) and DCCI (4.4 equivalents) in dichloromethane was added, followed by N-methylmorpholine (2 equivalents). The neutralisation of the resin in the presence of preactivated BOC-aminoacid eliminated the slight peptide loss from the resin which is sometimes observed in the base wash and coupling steps of the usual solid phase method, and improved the quality of the crude product. BOC-glycine was added similarly in the third and fourth cycles of synthesis; but in the fifth cycle after acid deprotection the resin was twice neutralised in a separate base wash stage with triethylamine in dichloromethane, and BOC-tyrosine coupled using DCCI in the presence of 1-hydroxy-benzotriazole. Each coupling was performed for two hours and its completeness checked using the fluorescamine test.

Over 90% cleavage of the peptide from the resin occurred, with no sulphoxidation, when the completed peptide resin was treated with 50% dimethylaminoethanol in DMF for two days. Hydrolysis at pH 9.7 of the labile peptide ester generated in the transesterification step, followed by chromatography on Sephadex LH 20 in DMF, gave BOC-Tyr-Gly-Gly-Phe-Met-OH (I) in 58% overall yield based on the amount of methionine originally coupled to the resin.

Alternatively treatment of the pentapeptide I phenyl ester resin with ammonia in 1:1 methanol DMF mixture gave, after 2 days, a quantitative liberation of the corresponding peptide amide.

All peptides described herein had amino-acid analyses within 7% of theoretical value and were homogeneous by thin layer chromatography (tlc) in at least three different systems. Deprotection of peptide I with aqueous trifluoroacetic acid under nitrogen gave, after chromatography on Sephadex G25 SF in 50% aqueous acetic acid (containing 0.01% mercaptoethanol), the desired product in 48% overall yield. The methionine enkephalin obtained was shown to be chromatographically and biologically identical to authentic material prepared by conventional solution synthesis.

The following examples illustrate individual syntheses, Example 1 and Example 3 onwards being syntheses of compounds according to the invention and Example 2 being included for details of synthetic procedures.

EXAMPLE 1

Analogue III-H211
Structure:

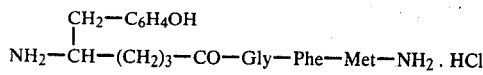

$$NH_2-CH-(CH_2)_3-CO-Gly-Phe-Met-NH_2 \cdot HCl$$
(with side chain $CH_2-C_6H_4OH$)

Synthesis:

(a) 5-tert.butoxycarbonyl amino-6-(4'-hydroxyphenyl)hexanoic acid

O-acetyl-N-phthaloyl-L-tyrosine (mp. 176°–179° C. $\tau(CDCl_3)$ 0.25 (1H,S,D$_2$O-exchangeable, COO$\underline{H}$), 2.33 (4H, multiplet, phthaloyl $\underline{H}$), $\tau_A$ 2.85, $\tau_B$ 3.13 (4H, A$_2$B$_2$, J=8 H$_z$, 2×ortho Ar$\underline{H}$), 4.80 (1H,t, J=8 H$_z$, α —C$\underline{H}$), 6.42 (2H,d,J=8 H$_z$, benzylic C$\underline{H}_2$), 7.80 (3H,S, 6COC$\underline{H}_3$). $\nu$mas (CHCl$_3$) 1780, 1750 br., 1720, 1390 cm$^{-1}$ was put through three cycles of Arndt-Eistert synthesis. The phthaloyl and acetoxyl groups were removed by acid hydrolysis and the desired product obtained after reaction with tert.butoxycarbonyl-azide. $\tau$CDCl$_3$ 1.80 br. D$_2$O exchangeable, COO$\underline{H}$), $\tau_A$ 3.02 $\tau_B$ 3.26 (4H, A$_2$B$_2$, J=9 H$_z$, 2×ortho Ar$\underline{H}$), ~5.3–6.5 (complex, partially D$_2$O-exchangeable, urethane N$\underline{H}$ and δ-C$\underline{H}$), 7.40 (2H,d,J=8 H$_z$, benzylic C$\underline{H}_2$) ~7.5–9.0 (6H, complex, 6×C$\underline{H}_2$ partly obscured by BOC Bu$^t$), 8.65 (9H,S,BOC-Bu$^t$) $\nu$max CHCl$_3$: 3600, 3440, ~2600 very br., 1710, 1515 cm$^{-1}$. Found: M (mass spec.) 323; C$_{17}$H$_{25}$NO$_5$ requires M 323.

(b) 5-tert.-butoxy-carbonylamino-6-(4'-hydroxyphenyl)hexanoyl-glycyl-L-phenylalanyl-L-methionine phenyl ester resin tert.Butoxycarbonyl-L-phenylalanyl-L-methionine phenyl ester resin (II (b) below, 0.33 g, 0.1 m mol) was subjected to the TFA deprotection, 0.075 M HCl in DMF exchange step described there. tert-Butoxycarbonylglycine (70 mg, 0.4 m mole) in CH$_2$Cl$_2$ (2.5 ml) was treated with DCCI (0.45 m mole) and added to the resin followed by N-methyl morpholine. After one hour the resin was thoroughly washed and shown to give a negative fluorescamine test. Acid deprotection (50% TFA) steps were followed by treatment with 10% triethylamine in CH$_2$Cl$_2$ (positive fluorescamine test). After thorough washing

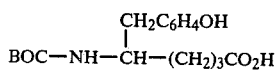

$$BOC-NH-CH-(CH_2)_3CO_2H$$
(with side chain $CH_2C_6H_4OH$)

(32 mg, 0.1 m mole) in 1:1 CH$_2$Cl$_2$/DMF (3 ml) containing 1-hydroxybenzotriazole (34 mg, 0.2 m mole) was treated with DCCI (0.15 m mole) and the mixture added to the resin and allowed to react overnight. The resin was thoroughly washed and then dried to give 0.36 g.

(c) 5-Amino-6-(4'-hydroxyphenyl)-hexanoyl-glycyl-L-phenylalanyl-L-methionine amide The completed analogue phenyl ester resin (0.36 g) was converted to its amide and purified as described below (II (d)). Fractions 44-46 gave 41.7 mg of gelatinous white solid, sparingly soluble in methanol, very soluble in trifluoroethanol. Tlc (silica gel) n-butanol/acetic acid/H$_2$O (3:1:1) Rf 0.71; ethyl acetate/pyridine/acetic acid/H$_2$O (80:20:6:1) Rf 0.94. The BOC-peptide analogue was deprotected under nitrogen with 80% trifluoroacetic acid, and the product chromatographed on Sephadex G25 SF as described there for (II). Fractions 28-29 were combined, evaporated and lyophilised from HCl, 25 mg of white fluffy solid. Tlc (silica gel) (i) Rf 0.50 ethyl acetate/pyridine/acetic acid/H$_2$O (60:20:6:11) (ii) Rf 0.51 n-butanol/acetic acid/H$_2$O (3:1:1); (iii) Rf 0.48 nPrOH/H$_2$O (7:3); Homogeneous by electrophoresis.

Amino acid analysis 6 N HCl+phenol, 110° C. 18 hours gives Met 0.92; Gly 1.01; Phe 0.99 (peptide content 90%)

EXAMPLE 2

Analogue II-H212
Structure:

H-Tyr-NH-(CH$_2$)$_4$-CO-Phe-Met-NH$_2$.HCl

Synthesis:

(a) tert.butoxycarbonyl-5-amino-pentanoic acid

5-Amino pentanoic acid (0.585 g, 5 m mol) was stirred for two days in dimethylformamide (5 ml) containing tetramethylguanidine (1.14 g, 10 m mol) and tert.butoxycarbonylazide (1.1 g, 7.5 m mol). The solution was evaporated and the residue partitioned between ethyl acetate (20 ml) and 10% citric acid solution (20 ml). The organic layer was washed with 10% citric acid (2×15 ml), water (3×15 ml) and brine 1×15 ml). Each aqueous wash was back extracted with ethyl acetate (20 ml). The combined organic layers were dried over anhydrous magnesium sulphate and evaporated to give an oil which slowly crystallised. Recrystallisation from diisopropyl ether/petrol gave 0.745 g (70% yield), mp. 47.5°–48.5° C., Rf silica gel 0.40 (benzene:dioxan:acetic acid 95:75:4).

(b) tert.butoxycarbonyl-L-phenylalanyl-L-methionine phenyl resin ester

The acetoxy resin (1.4% cross linked, 10 mole percent acetoxy-styrene) (1.0 g) was placed in the synthesis apparatus and stirred overnight with dimethylformamide:dioxan:hydrazine hydrate (10:5:1). The resin was repeatedly washed with each of the following DMF, DMF/H$_2$O (3:1), DMF, CH$_2$Cl$_2$, isopropanol, CH$_2$Cl$_2$. BOC-methionine (500 mg, 2 m mol) in dichloromethane (7.5 ml) was treated with dicyclohexylcarbodiimide (0.51 g, 2.47 m mol) and the mixture added to the resin followed by pyridine (1 ml). The coupling was allowed to stir for 3 hours; then the resin was thoroughly washed: CH$_2$Cl$_2$ (3×), iPrOH(3×), CH$_2$Cl$_2$ (3×), DMF (3×). Unreacted phenolic hydroxyl groups were acetylated by treating with acetic anhydride (1 g) and triethylamine (1.4 ml, 10 m mol) in DMF (10 ml). This was performed for ninety minutes, and then repeated again after further washing. Amino acid analysis showed 0.4 m mol/gram methionine added on to resin. The resin was then thoroughly washed and treated with 50% trifluoroacetic acid in CH$_2$Cl$_2$ (containing 2% ethanedithiol and 2% diethyl phosphite). Deprotection was for 1 minute followed by treatment for 15 minutes. This doubled treatment was again repeated after CH$_2$Cl$_2$ (3×), iPrOH (3×) and CH$_2$Cl$_2$ (3×) washes. The resin was again washed thoroughly and a small sample shown to give a strongly positive fluorescamine test. The resin was then twice washed with 0.075 M HCl in DMF (10 ml for 2 minutes each time). This exchange process was repeated after thorough washing. The resin was again thoroughly washed and treated with a solution of tert.butoxycarbonyl-L-phenylalanine (0.43 g, 1.6 m mol) in $CH_2Cl_2$ (7 ml) to which had been added DCCI (0.36 g, 1.75 m mol). The stirred suspension was then neutralised in situ by the addition of N-methyl morpholine (80 μl). After one hour the resin was thoroughly washed and shown to give a negative fluorescamine test.

(c) BOC-L-tyrosyl-5-aminopentanoyl-L-phenylalanyl-L-methionine phenyl ester resin A sample of the dipeptide resin from (b) (0.32 g, 0.1 m mol) was deprotected and exchanged as in the coupling cycle described above. The thoroughly washed resin was treated with a solution of tert.butoxycarbonyl-5-aminopentanoic acid (0.114 g, 0.5 m mol) in $CH_2Cl_2$ (2.5 ml) to which had been added DCCI (0.6 m mol) The stirred suspension was neutralised in situ by the addition of N-methyl morpholine (20 μl). After one hour the resin was thoroughly washed and shown to give a negative fluorescamine test. Deprotection of the peptide resin was performed as before with 50% trifluoroacetic acid in $CH_2Cl_2$ containing 2% diethylphosphite and 2% ethane dithiol. After thorough washing the resin was treated with 10% triethylamine in $CH_2Cl_2$ (2×2 minutes). A sample was shown to give a positive fluorescamine test. The resin was again thoroughly washed and then treated with a solution of BOC-L-tyrosine (93 mg, 0.33 m mol) and 1-hydroxybenzotriazole hydrate (110 mg, 0.65 m mol) in 50% $CH_2Cl_2/DMF$ (3 ml) to which had been added DCCI (0.6 m mol). After three hours reaction the resin was thoroughly washed and gave a very weakly positive fluorescamine test.

(d) L-Tyrosyl-5-aminopentanoyl-L-phenylalanyl-L-methionine amide

The total resin from (c) was suspended in 1:1 methanol/DMF (20 ml) and saturated at 0° C. with anhydrous ammonia. After two days at room temperature the suspension was filtered and the resin beads thoroughly washed with DMF. The combined filtrates were evaporated in vacuo to give an oily residue (137 mg, weight resin recovered 220 mg). This was dissolved in the minimum volume of dimethylformamide and applied to a column of Sephadex LH20 (94×2.5 cm). The column was eluted with DMF at a flow rate of 20 ml/hour collecting 190 drop (6 ml) fractions. Fractions 43-46 were combined and evaporated to give 77 mg. of white solid, sparingly soluble in methanol, very soluble in trifluoroethanol. Tlc (silica gel): n-butanol/acetic acid/$H_2O$ (3:1:1) Rf 0.73; ethyl acetate/pyridine/acetic acid/$H_2O$ (80:20:6:11) Rf 0.94; ethyl acetate/n-butanol/acetic acid/$H_2O$ (1:1:1:1) Rf 0.79; nPrOH/$H_2O$ (7:3) Rf 0.71. The BOC-peptide analogue was treated under nitrogen for 30 minutes with 80% trifluoroacetic acid. The solution was evaporated and the residue dissolved in deaerated 50% acetic acid containing 0.01% mercaptoethanol. The solution was applied to a column of Sephadex G 25 SF and it was eluted with the system at 8 ml/hour collecting 130 drop (4 ml) fractions. Fractions 29-31 were combined and evaporated to give a residue which on lyophilisation gave 50.7 mg of white fluffy solid; tlc (silica gel): (i) Rf 0.56 ethylacetate/pyridine/acetic acid/$H_2O$ (60:20:6:11); (ii) Rf 0.54 N butanol/acetic acid/$H_2O$ (3:1:1); (iii) Rf 0.49 NPrOH/$H_2O$ (7:3); homogenous by electrophoresis; amino acid analysis 6 N HCl+phenol, 110° 18 hours gives Met 0.95; Tyr 1.04, Phe 1.02 (peptide content 85%). Lyophilisation from dilute hydrochloric acid afforded the hydrochloride.

EXAMPLE 3

Analogue—H215
Structure:

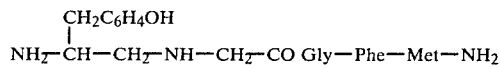

Synthesis:

(a) t.butoxycarbonyl-O-t.butyl-L-tyrosyl glycine t.butyl ester

N-t.butoxycarbonyl-O-t.butyl-L-tyrosine (2 g, 6.15 mmol) was dissolved in dimethylformamide (15 ml) and the stirred solution treated at −15° with N-methyl morpholine (0.67 ml, 6.15 mmol) and iso-butylchloroformate (0.81 ml, 6.15 mmol). After 10 minutes a precooled mixture of glycine t.-butyl ester dibenzenesulphimide salt (2.64 g, 6.15 mmol) and triethylamine (0.86 ml, 6.15 mmol) in dimethylformamide (5 ml) was added. The mixture was stirred at −10° for 30 minutes, allowed to warm to room temperature and left overnight. The reaction mixture was poured into ice cold 1 M citric acid solution; and extracted with ethyl acetate (2×50 ml). The combined organic layers were washed with 1 M citric acid (2×25 ml), saturated sodium bicarbonate solution (3×25 ml) and with saturated brine (2×50 ml). The organic layer was dried over anhydrous magnesium sulphate and evaporated to give an oily residue. The residue was extracted with 40°-60° petroleum ether (50 ml). After 1 hour at 4° the supernatant liquor was decanted and evaporated. The oily residue was again extracted as previously; evaporation gave 1.13 g (41%) as an oily gum, tlc (silica gel): Rf 0.65 chloroform/methanol (95:5); Rf 0.59 benzene/dioxan/acetic (95:25:4). τ (CDCl₃) $τ_A$2.84, $τ_B$3.08 (4H, $A_2B_2$, J=9 Hz, 2×ortho Ar H̲), ~3.55 (1H, broad, $D_2O$ exchangeable, amide NH̲), 4.85 (1H,α, J=8 Hz, $D_2O$ exchangeable, urethane NH̲), 5.60 (1H, multiplet, α —CH), 6.12 (2H, d, J=6 Hz, Gly CH̲₂), 6.97 (2H, d, J=7 Hz, Tyr β —CH̲₂), 8.55, 8.60 and 8.70 (27H, S, Boc ᵗBu̲, COOᵗBu̲ and Oᵗ Bu̲).

(b) N-t.butoxycarbonyl-N-[2-t.butoxycarbonylamino, 3 (4′-t.butoxyphenyl) propyl]glycine Boc-Tyr(ᵗBu)-Gly-Oᵗ Bu (1.13 g, 2.5 m mol) was azeotroped with benzene and thoroughly dried. The meringue like residue was dissolved in benzene (15 ml) and treated with 70% solution of sodium dihydrobis-(2-methoxyethoxy) aluminate (5 ml, 17 m mol). The mixture was heated at 83° for 1 hour, then cooled to 0° and carefully poured into ice cold 10% citric acid solution (70 ml). The solution was neutralised to pH 8 with solid sodium carbonate and extracted with ether (3×60 ml). The combined ether layers were washed with ice cold 10% citric acid (3×70 ml). The combined aqueous extracts were neutralised to pH 8.5 and extracted with ether (3×100 ml) The combined ether layers from this extraction were dried over anhydrous magnesium sulphate and evaporated to give 0.65 g (71%) of the reduction product; tlc silica gel: Rf 0.44 ethyl acetate/pyridineacetic acid/$H_2O$ (60:20:6:11); Rf 0.04 benzene/dioxan/acetic (95:25:4).

τ(CDCl₃) $τ_A$2.90 $τ_B$3.12 (4H, $A_2B_2$, J=9 Hz, 2×ortho Ar H), 5.3 (1H, broad, $D_2O$-exchangeable, urethane NH̲), ~6.2 (1H multiplet, —CH̲), 7.10-7.50 (6H, complex, 3×CH̲₂), 8.58 and 8.68 (18H,S, Boc ᵗBu̲ and O-ᵗBu̲).

Approximately half the product (0.32 g, 0.9 m mol) was stirred for 4 days at room temperature in 1:1 dioxan/1 M potassium bicarbonate in the presence of t. butoxycarbonylazide (0.28 g, 2 m mol). The solvents were evaporated and the residue partitioned between ether (30 ml) and water (20 ml). The ether layer was washed with water (2×20 ml) and saturated brine (2×20 ml). Each aqueous wash was back extracted with ether (20 ml). The ether solutions were further washed with ice cold 10% citric acid solution (3×20 ml), water (2×20 ml) and brine (1×10 ml). The pooled ether solutions were dried over magnesium sulphate and evaporated to give 0.27 g (63%); tlc (silica gel): Rf 0.46 benzene/dioxan/acetic acid (95:25:4); Rf 0.42 chloroform/methanol (95:5).

τ(CDCl₃) τ$_A$ 2.95, τ$_B$ 3.15 (4H, A₂B₂, J=9 Hz, 2×ortho Ar H̲), 5.85-7.15 (5H, complex, CH̲ and 2 CH̲₂), 7.37 (2H, d, J=6 Hz, Ph CH̲₂), 8.58, 8.63 and 8.68 (27H, S, 2×Boc $^t$Bu̲ and O$^t$Bu̲).

Most of the tri-Boc derivative (0.26 g, 0.52 m mol) was dissolved in pyridine (5 ml); water (2.5 ml) and potassium permanganate (0.5 g) were added, and the mixture vigorously stirred for three days. The pyridine was evaporated and the residue partitioned between ethyl acetate (40 ml) and ice cold citric acid solution (30 ml). The organic layer was washed with citric acid, water and brine; each aqueous phase was back extracted with ethyl acetate. The combined organic layers were dried over magnesium sulphate and evaporated to give a residue (0.2 g). This crude product was dissolved in ether (20 ml) and extracted with 3% aqueous ammonia (4×15 ml); each extract was back washed with ether (15 ml). The combined aqueous phases were acidified to pH 3 with solid citric acid and extracted with ethyl acetate (50 ml, 25 ml). The combined organic phases were washed with water and brine, then dried over magnesium sulphate and evaporated. The residue (122 mg) was applied to a preparative silica plate and run in benzene/dioxan/acetic acid (95:25:4). The gel bands corresponding to the two U.V. absorbing products were scraped from the plates and thoroughly extracted with ethyl acetate. The organic phases were evaporated. The top band (Rf 0.47) was identified as 4-t.butoxy-benzoic acid: the lower band (Rf 0.32) as the required product 57 mg (22%); tlc (silica gel): Rf 0.47 benzene/dioxan/acetic (95:25:4); Rf 0.05 chloroform/methanol (95:5). τ(CDCl₃) 1.30 (1H, broad, COOH̲), τ$_A$ 2.95, τ$_B$ 3.18 (4H, A₂B₂, J=9 Hz, 2×ortho Ar H̲), ~5.85-~7.1 (5H, complex CH̲ and 2CH̲₂), 7.30 (2H, d, J=6 Hz, benzylic CH̲₂), 8.60, 8.65 and 8.70 (27H, S, 2 Boc $^t$Bu̲ and O$^t$Bu̲).

(c) N-[2-amino, 3-(4'-hydroxyphenyl)propyl]glycyl-glycyl-L-phenylalanyl-L-methionine amide (H215)

Starting from Boc-methionine phenyl ester resin (0.364 g, 0.15 m mol); glycyl-L-phenylalanyl-L-methionine phenyl ester resin was prepared as described in Example 1. After thorough washings,

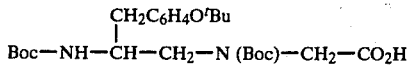
Boc—NH—CH—CH₂—N (Boc)—CH₂—CO₂H (47 mg, 0.095 m mol) in 1:1 CH₂Cl₂/DMF (2 ml) containing 1-hydroxy benzotriazole (34 mg, 0.2 m mol) was treated with DCCI (0.15 m mol) and the mixture added to the resin and thoroughly stirred overnight. The resin was washed with DMF (3×), CH₂Cl₂ (3×), isopropanol (3×), CH₂Cl₂ (3×); 10% triethylamine in CH₂Cl₂ (2×), and CH₂Cl₂ (4×). Remaining amino groups were blocked by reaction with acetyl imidazole (0.2 g, 2 m mol) in DMF (5 ml) for 1 hour. The resin was thoroughly washed with DMF, CH₂Cl₂, isopropanol, CH₂Cl₂ and methanol. The dried resin weighed 0.413 g.

One half of the resin (0.206 g) was stirred at 0° in 1:1 methanol/DMF (20 ml). The suspension was saturated with anhydrous ammonia; the flask tightly stoppered and stirred at room temperature for two days. The suspension was filtered and the resin beads washed with 1:1 methanol/DMF and then DMF. The combined filtrates were evaporated and the residue redissolved in DMF (1 ml). The solution was applied to a column of Sephadex LH 20 (90×2.5 cm), and eluted with DMF at a flow rate of 15 ml/hr collecting 190 drop (6 ml) fractions. Fractions 36-39 were pooled and evaporated to give 30.9 mg of pure protected peptide, tlc (silica): Rf 0.5 choroform/methanol (9:1), Rf 0.95 EtOAc/n-butanol/acetic acid/H₂O (2:1:1:1).

The protected peptide was dissolved in 80% trifluoroacetic acid under nitrogen. After 2 hours the solvents were evaporated in vacuo and the residue chromatographed on a column of Sephadex G25 SF (95×1.5 cm) in 50% deaerated acetic acid (containing 0.01% mercaptoethanol) at 12 ml/hr collecting 130 drop (4 ml) fractions. Fractions 24-28 were combined and evaporated to give 22 mg of peptide. This was dissolved in deaerated 0.01 M ammonium acetate pH 7 (1 ml) and applied to a column (40×1 cm) of Whatman CM 52. The column was eluted at 10 ml/hr with 0.01 M buffer collecting 70 drop (4.3 ml) fractions. After the first fraction a linear gradient over two days to 0.2 M ammonium acetate was commenced. Fractions 38-41 were pooled and lyophilised to give 9.6 mg; tlc (silica gel) Rf 0.40 ethyl acetate/pyridine/acetic acid/water (60:20:6:11), Rf 0.64 ethyl acetate/n-butanol/acetic acid/H₂O (1:1:1:1).

Amino acid analysis: 4 M CH₃SO₃H 115° 24 hours Peptide content 86% Gly 1.03, Phe 0.97, Met 1.00 (determined in a parallel 6 N HCl hydrolysis).

EXAMPLE 4

Analogue—H216
Structure:

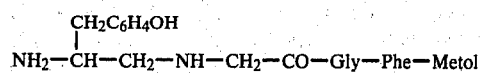
NH₂—CH—CH₂—NH—CH₂—CO—Gly—Phe—Metol

Synthesis:

The protected isostere peptide resin (see H215, section C; 0.206 g) was stirred for 2 days in 1:1 methanol/DMF (20 ml) in the presence of triethylamine (1 ml). The suspension was filtered and the resin beads thoroughly washed with 1:1 methanol/DMF, and then DMF. The combined filtrates were evaporated and the residue chromatographed on a column (90×2.5 cm) of Sephadex LH20 in DMF eluted at a flow rate of 15 ml/hr collecting 190 drop (6 ml) fractions. Fractions 38-40 were combined and evaporated to give 23.3 mg of the peptide methyl ester; tlc silica gel: Rf 0.9 ethyl acetate/n-butanol/acetic acid/water (2:1:1:1), Rf 0.66 chloroform/methanol (9:1).

The peptide was dissolved in methanol (1 ml). Water (1 ml) and sodium borohydride (37 mg) were added and the mixture stirred overnight; tlc showed in chloroform/methanol (9:1) complete reduction—new spot at Rf 0.5, no spot at RF 0.66. The solvents were evaporated and the dried residue treated under nitrogen with 80% trifluoroacetic acid. After 2 hours the solvents were evaporated and the residue dried in vacuo.

The residue was dissolved in deaerated 50% acetic acid and chromatographed on a column (95×1.5 cm) in 50% deaerated acetic acid (containing 0.01% mercaptoethanol) at 12 ml/hr collecting 130 drop (4 ml) fractions. Fractions 23-27 were combined and evaporated to give a residue of 22 mg. This was dissolved in deaerated 0.01 M ammonium acetate pH 7 and applied to a column (40×1 cm) of Whatman CM52. The column was eluted at 10 ml/hr with 0.01 M buffer collecting 70 drop (4.3 ml) fractions. After the first fraction a linear gradient over two days to 0.2 M ammonium acetate pH 7 was commenced. Fractions 39-43 were pooled and lyophilised to give 9.6 mg; tlc (silica gel): Rf 0.42 ethylacetate/pyridine/acetic acid/water (60:20:6:11); Rf 0.66 ethyl acetate/n-butanol/acetic acid/water (1:1:1:1).

Amino acid analysis: 4 M methane sulphonic acid 115° 24 hours. Peptide content 100% Gly 1.07, Phe 0.93, methionine absent.

EXAMPLE 5

Analogue—H222
Structure:

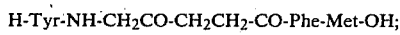

H-Tyr-NH-CH₂CO-CH₂CH₂-CO-Phe-Met-OH;

Name: 5-(N-Tyrosylamino), 3-oxopentanoyl-L-phenylalanyl-L-methionine

Synthesis:

(a) 4-(N-t.butoxycarbonylamino), 4-oxopentanoic acid

Boc-glycine (1.26 g, 7.2 m mol) and N-methylmorpholine (0.79 ml, 7.2 m mol) in ethyl acetate (30 ml) were treated at −10° with iso-butylchloroformate (0.95 ml, 7.2 m mol). After seven minutes the suspension was filtered into an ice cold flask and the precipitate washed with precooled ethyl acetate (5 ml). A solution of diazomethane in ether (15.8 m mol in 150 ml) was added, and the solution kept at 4° C. overnight. Evaporation of the solvents gave diazoketone (I) (see Scheme 1 below). I.R. spectrum $v_{max}$(CHCl₃) 2100 cm⁻¹. One half of this product in ethyl acetate (36 ml) was treated with 0.07 M hydrogen bromide in ethyl acetate (56.5 ml, 4 m mol). The solvents were evaporated and the bromoketone (II) dried thoroughly over potassium hydroxide in vacuo. Most of the product (3.2 m mol) was treated in dry benzene (6.5 ml) with triethylamine (20 μl) and then with triphenylphosphine (0.85 g, 3.24 m mol). The solution was stirred overnight at room temperature. The solvent was evaporated and the pure keto-triphenylphosphonium bromide (III) (1.00 g, 60% overall) obtained as white crystals from methanol/ether; m.p. 111°-115° C. (with decomp); $v_{max}$ (CHCl₃): 1725, 1695 cm⁻¹; τ(CDCl₃): 2.33 (15H, multiplet, PPh₃), ca. 3.0-4.5 (3H, complex, D₂O-exchangeable, NH and COCH₂), 5.70 (2H,d,J=6 Hz, CH₂), 8.6 (9H, s, Boc t Bu).

A suspension of (III) (0.51 g) in ethyl acetate (10 ml) was stirred vigorously overnight with 1 M sodium carbonate solution (10 ml). The organic layer was separated and the aqueous phase again extracted with ethyl acetate. The combined extracts were washed with saturated brine, dried, and evaporated in vacuo to give the pure yields (IV) as a white crystalline solid (0.43 g, 100%); $v_{max}$(CHCl₃): 1700, 1545 cm⁻¹; τ(CDCl₃): 2.57 (15 H, multiplet, PPH₃), 4.60 (1H, br., D₂O-exchangeable, NH), 6.10 (2H, d, J-5 Hz, CH₂), 6.65 (1H, br., COCH), 8.59 (9H, s, Boc-t Bu).

A solution of ylid (IV) (0.32 g, 0.74 m mol) and ethyl bromoacetate (1.23 g, 7.4 m mol) in dry DMF (7.40 ml) was stirred vigorously under N₂ at 80° C. for 2 hours with anhydrous sodium carbonate (1.51 g). The DMF was evaporated in vacuo and the residue partitioned between ethyl acetate and water. The organic phase was washed with water and saturated brine, then dried and evaporated in vacuo to give a pale yellow gum. The material was purified by preparative thin layer chromatography using ethyl acetate/acetone/benzene (1:2:3) for development. Elution with ethyl acetate afforded pure ylid (V) as an almost colourless gum (0.074 g, 20%); $v_{max}$(CHCl₃): 1725, 1700, 1537 cm⁻¹; τ(CDCl₃): 2.48 (15H, multiplet, PPh₃), 4.26 (1H, br., D₂O-exchangeable, NH), 5.6-6.1 (6H, complex, 2×CH₂ and COOCH₂CH₃), 8.60 (9H, s, Boc t Bu), 8.90 (3H, t, J=7 Hz, COOCH₂CH₃). The total product (0.145 m mol) was converted into its hydrochloride and electrolysed in 1:1 acetonitrile/deaerated water (30 ml) under N₂ at 25 V using mercury and platinum electrodes. After 1 hour at room temperature the solution was evaporated and the residue chromatographed on a column (67×3.2 cm²) of Sephadex LH20 using methanol as eluant. The keto-ester (V) eluted in fractions 49-51 (the column was run at 12 ml/h collecting 6 ml fractions); tlc: Rf 0.53, benzene/dioxan/acetic acid (95:25:4). The product was dissolved in methanol (0.72 ml) and saponified for 2 hours at room temperature by the addition of 0.2 M sodium hydroxide solution. Pure keto-acid VI was obtained after acidification and extraction as a white solid (0.019 g, 57% over the last two steps); tlc (silica) Rf 0.39 benzene/dioxan/acetic acid (95:25:4); τ(CDCl₃): 1.12 (1H, S, D₂O-exchangeable, COOH), 4.55 (1H, br, D₂O-exchangeable, NH), 5.87 (2H, d, J=5.5 Hz, NH—CH₂), 7.27 (4H, S, 2×CH₂), 8.55 (9H, S, Boc t Bu).

A summary of the above procedure is given in Scheme 1 below, which is Summary Scheme 'A' where R¹=R²=H. Scheme 2 which follows it is an alternative, particular synthesis.

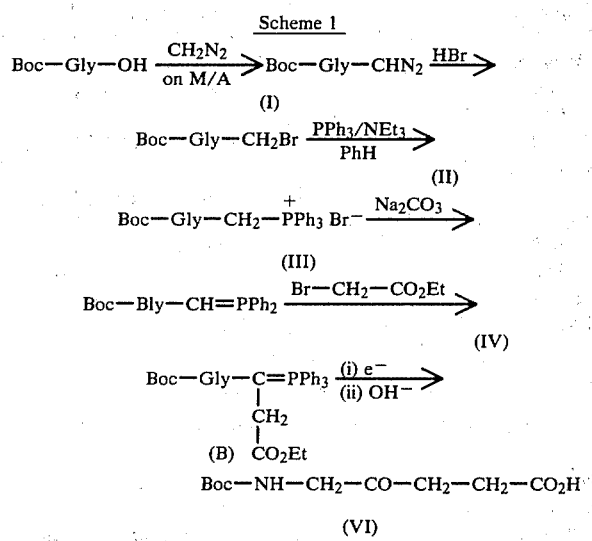

The above is a generally applicable method. A synthesis of (VI) by alternative non-general route is as follows. As shown in Scheme 2 below succinic anhydride is heated in dry ethanol to afford a half ester. The resulting mono-acid function is transformed into its diazoketone by the action of diazomethane on the mixed anhydride, and this is then converted to the bromoketone, these last two reactions being performed similarly to analogous reactions previously described. Treatment of the bromoketone with potassium phthalimide in DMF at 60° gives the phthalimido-ester which can be converted to the desired keto-acid (IV) by acidic hydrolysis followed by reprotection by reaction with Boc-azide.

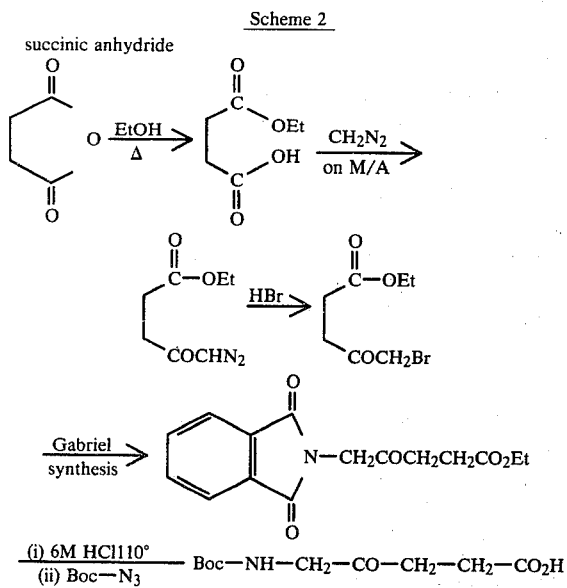

Scheme 2

(b) Synthesis of H-Tyr-NH-CH$_2$-CO-CH$_2$-CH$_2$-CO-Phe-Met-OH

Starting from Boc-methionine phenyl ester resin (0.205 g, 0.082 m mol), Boc-Phe-Met-resin was prepared as described in Example 2, (b) and (c). After deprotection as usual, and treatment with 10% triethylamine in CH$_2$Cl$_2$ the free base from resin gave a positive fluorescamine test. Boc-NHCH$_2$COCH$_2$CH$_2$CO$_2$H (VI, 19 mg, 0.082 m mol) and 1-hydroxylbenzotriazole (27.5 mg, 0.16 m mol) in 1:1 CH$_2$Cl$_2$/DMF (2.5 ml) were treated with DCCI (0.12 m mol) and added to the resin. The incorporation of isostere was allowed to proceed overnight. The resin still gave a positive fluorescamine test and was acetylated with acetyl imidazole (fluorescamine test negative). After acid deprotection using doubled treatment with 50% trifluoroacetic acid in CH$_2$Cl$_2$ containing 2% diethyl phosphite only, a positive fluorescamine test was obtained indicating successful incorporation. Boc-L-tyrosine was added, as previously, in the last cycle of synthesis (fluorescamine test negative). The resin was stirred for 2 days in 1:1 dimethylaminoethanol/DMF (20 ml). The suspension was filtered and the beads thoroughly washed with DMF. The combined filtrates were evaporated in vacuo and the residue dissolved in 1:1 DMF/water (16 ml). The solution was maintained at pH 9.7 overnight by the addition of 0.1 M sodium hydroxide solution. Water (8 ml) was added and the mixture acidified to pH 3.2 by the addition of potassium bisulphate solution. The solution was evaporated to dryness in vacuo and the residue extracted into a small volume of DMF which was chromatographed on Sephadex LH 20 in DMF (as described in Example 3, (c). Fractions 43-46 were pooled and evaporated in vacuo to give 16.2 mg of the Boc-peptide;

tlc (silica): Rf 0.75 ethyl acetate/pyridine/acetic acid/water (60:20:6:11). The total product was dissolved in 80% aqueous trifluoroacetic acid under nitrogen. After 30 minutes the solution was evaporated in vacuo and the residue chromatographed on Sephadex G25 SF as described in Example 3, (c). Fractions 26-29 were pooled, evaporated and the residue further purified on a column (1×32 cm) of SP Sephadex C25 (triethylamine form) eluted at 10 ml/hr collecting 100 drop fractions with a linear gradient from 0.01 M triethylamine formate pH 5 to 0.5 M triethylamine formate pH 6.9. The desired product (7 mg) was isolated from fractions 13-14 by lyophilisation: tlc (silica) Rf 0.32 (ethyl acetate/pyridine/acetic acid/water (60:20:2:11).

Amino acid analysis 6 M HCl 110° 18 hours, peptide content 80%, Tyr 0.50; Phe 1.03; Met 0.97.

EXAMPLES 6 TO 8

Analogues—H218, H219 and H220
Structures:

H218
H-Tyr-NH-CH$_2$-CH$_2$-NH-CH$_2$-Co-Phe-Met-OH

H219
H-Tyr-NH-CH$_2$-CH$_2$-NH-CH$_2$-CO-Phe-Metol

H220
H-Tyr-NH-CH$_2$-CH$_2$-NH-CH$_2$-CO-Phe-Met-NH$_2$

Synthesis:
(a) N-benzyloxycarbonyl-N-(2-t.butoxycarbonylaminoethyl)glycine

2-Bromo-N-t.butoxycarbonylaminoethane (prepared by treatment of 2-bromoethylamine hydrochloride with Boc-azide and triethylamine in DMF; 0.9 g, 4 m mol) was stirred in dry DMSO (10 ml) with glycine ethyl ester hydrochloride (1.4 g, 10 m mol) and triethylamine (1.95 ml, 14 m mol) for 2 days at 37°. The mixture was partitioned between 1 M sodium bicarbonate and ethyl acetate, and the organic extract dried and evaporated. Purification on Sephadex LH 20 in methanol (as described above) gave from fractions 25-26 N-(2-t.butoxycarbonylaminoethyl) glycine ethyl ester (0.31 g, 32% yield); tlc Rf 0.54 butanol/acetic acid/water (3:1:1). A sample (0.25 g, 1 m mol) was stirred with benzyl chloroformate (0.17 ml, 1.5 m mol) in dioxan (5 ml) and 1 M potassium bicarbonate solution (5 ml) at room temperature overnight. Excess reagent was destroyed by reaction with unsym.-dimethylethylenediamine (0.11 ml, 1.00 m mol) for 1 hour, and the product ethyl ester isolated by ethyl acetate extraction of the acidified reaction mixture. Hydrolysis in methanol (15 ml) with 0.2 M sodium hydroxide solution (0.5 ml) gave, after recrystallisation from ethyl acetate—60°-80° petroleum ether, the desired derivative 0.23 g (61% for last 2 steps); mp. 91.5°-94°, tlc (silica) Rf 0.22 benzene/dioxan/acetic acid (95:25:4), Rf 0.05 chloroform/methanol (9:1).

(b) Boc-Tyr-NH-CH$_2$-CH$_2$N(Z)CH$_2$CO-Phe-Met phenolic resin ester (Z=benzyloxycarbonyl; Boc=t-butoxy carbonyl as before)

Boc-methionine phenyl ester resin (0.555 g, 0.22 m mol) was doubly deprotected (as usual), and after thorough washing (fluorescamine test positive), treated with 10% triethylamine in CH$_2$Cl$_2$ (4×20 secs). After rapid washing, there is added immediately a solution prepared 2 minutes previously at 4° of Boc-phenylalanine (0.265 g, 1 m mol) and HOBt (0.34 g, 2 m mol) in 1:1 DMF/CH₂Cl₂ (7 ml) treated with DCCI (0.22 g, 1.1 m mol). After 90 minutes the resin was washed with DMF (3×), CH₂Cl₂ (3×), iPrOH (3×) CH₂Cl₂ fluorescamine test negative). The resin was washed with 10% triethylamine in CH₂Cl₂ (4×20 seconds), thoroughly washed and reacted with acetyl imidazole (0.3 g, 3 m mol) in DMF (7 ml). After 30 minutes the resin was washed as after coupling step. In the next cycle the resin was doubly deprotected, washed (fluorescamine test positive) and repeatedly treated with 10% triethylamine in CH₂Cl₂ (4×20 seconds). After rapid washing, there was immediately added a solution of Boc-NH-CH₂-CH₂-N(Z)-CH₂-CO₂H (100 mg, 0.28 m mol) and HOBt (96 mg, 0.56 m mol) in 1:1 DMF/CH₂Cl₂ (5 ml) at 0° treated 2 minutes previously with DCCI (83 mg, 0.4 m mol). The reaction was left overnight. After thorough washing the fluorescamine test was faintly positive. The resin was treated with 10% triethylanine in CH₂Cl₂ (4×20 seconds), thoroughly washed and reacted for 1 hour with acetyl imidazole. The resin was washed (fluorescamine test negative) and deprotected with 25% trifluoroacetic acid in CH₂Cl₂ containing 2% ethanedithiol and 2% diethyl phosphite (for 1 minute, and then for 30 minutes). After thorough washing (fluorescamine test positive) the resin was treated with 10% triethylamine in CH₂Cl₂ (4×20 seconds), rewashed, and then Boc-tyrosine (0.29 g, 1 m mol) was coupled as previously. The resin was washed thoroughly (fluorescamine test negative) and dried to give 0.707 g.

(c) H 218: One third of the resin was treated with dimethylaminoethanol and the labile peptide ester hydrolysed as described previously. After chromatography on Sephadex LH 20 in DMF the peptide acid was deprotected for 30 minutes in liquid HF at 0° in the presence of amisole (1 ml) and methionine (100 mg). Chromatography on Sephadex G25 SF and Whatman CM 52 gave 14.8 mg of H218; tlc Rf 0.54 ethyl acetate/pyridine/acetic acid/H₂O (50:20:6:11), Rf 0.70 ethyl acetate/n butanol/acetic acid/water (1:1:1:1). Amino acid analysis: Tyr 1.00, Phe 1.01; Met 0.84; Aminoethylglycine 0.99.

(c) H219: A further third of the resin was treated which methanol and di-isopropylethyl amine to give the free peptide methyl ester which was reduced as described for H216. Chromatography and deprotection as for H218 gave 18.5 mg of the desired product; tlc (silica) Rf 0.67 ethyl acetate/pyridine/acetic acid/water (50:20:6:11), Rf 0.73 ethyl acetate (n butanol/acetic acid/water (1:1:1:1). Amino acid analysis, Tyr 1.01; Phe 0.94, Aeg 1.05, methionine absent.

(c) H220: Transamidation of the remaining resin and the usual chromatography and deprotection procedures gave 20 mg of H220, tlc (silica) Rf 0.65 ethyl acetate/pyridine/acetic acid/water (50:20:6:11), Rf 0.69 ethyl acetate 1 n butanol/acetic acid/water (1:1:1:1).

Amino acid analysis: Tyr 1.03, Phe 0.94, Met 0.99; Aeg 1.04.

EXAMPLE 9 H224

(1) Boc-Phe-Met-OMe

Boc-Phe-OH (0.95 g, 3.5 mmole) and HCl.H-Met-OMe (0.71 g, 3.6 mmol) were coupled together at 0° in CH₂Cl₂ in the presence of DCCI (0.81 g, 3.9 mmol) and NEt₃ (0.5 ml, 3.6 mmole). After 1 day the reaction mixture was worked up by normal acid-base wash procedures. Crystallisation from ether-40°-60° petrol gave 1.08 g (76%) fine needles, m.p. 70°-71°, t.l.c. (silica): Rf 0.83 chloroform/methanol (95:5); Rf 0.56 benzene/dioxan/acetic acid (95:25:4); NMR spectrum in accord τ (CDCl₃) 2.7 (5H multiplet, ArH), 3.4 (1H, d, J=8 Hz, D₂O exchangeable, amide NH), 4.9 (1H, d, J=7 Hz, D₂O exchangeable, urethane NH), 5.5 (2H, complex, 2x —CH), 6.3 (3H, S, —OCH₃), 6.95 (2H, d, J=6 Hz, Phe β —CH₂), 7.8 (4H, complex, —CH₂—CH₂—), 7.95 (3H, S, S—CH₃), 8.55 (9H, S, Boc 'Bu).

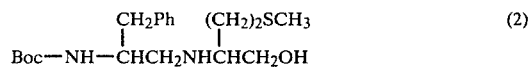

The dipeptide (1) (0.7 g, 1.7 mmol) in dry benzene (10 ml) was treated with 70% SDA solution in toluene (4 ml) at room temperature, then refluxed for 45 minutes. The mixture was cooled to 0° and added to ice cold 10% citric acid (50 ml), and then the whole mixture neutralised to pH 8 and extracted into ethyl acetate (3×). The combined washed organic phases were evaporated and the residue chromatographed on a 30×2.5 cm column of SP Sephadex C25 (Pyr form). The column was run in MeOH/nBuOH/H₂O (13:10:7) and eluted with 100 ml of this system, then 100 ml each of 20% pyridine and finally 1 M NEt₃. Evaporation of the triethylamine wash gave an oily residue which was crystallised from methanol/water to give 0.36 g (57%) of white needles; t.l.c. (silica) Rf 0.1 CHCl₃/MeOH (95:5), Rf 0.05 benzene/dioxan/acetic acid (95:25:4). Nmr: τ(CDCl₃) 2.75 (5H, multiplet, ArH), 5.25 (1H, d, J=8 Hz, D₂O exchangeable, urethane NH), 6.2 (2H, complex, 2×NH-CHCH₂), 7.9 (3H, S, SCH₃), 7.0-8.5 (11H, complex, 5×CH₂+NH).

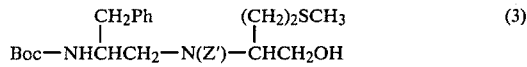

The reduced isostere (0.18 g, 0.49 mmol) and KHCO₃ (0.5 g, 5 mmol) were stirred at r.t. in peroxide-free dioxan (5 ml) and water (5 ml). Benzyl chloroformate (250 mg, 1.5 mmol) was added and the mixture stirred overnight. Unsymmetrical dimethylethylenediamine (0.16 ml, 1.5 mmol) was added and the mixture stirred for a further 6 hours. The solution was evaporated and partitioned between ethyl acetate and cold 10% citric acid. The organic layer was washed twice more with citric acid solution, once with water, twice with saturated sodium bicarbonate solution, dried and evaporated to give 270 mg (100%) of a colourless oil; t.l.c. (silica) Rf 0.71 chloroform/methanol (95:5); Rf 0.49 benzene/dioxan/acetic acid (95:25:4); Nmr: τ(CDCl₃), 2.5 (5H, s, C₆H₅CH₂—O—CO—), 2.6 (5H, multiplet, Phe ArH), 4.7 (2H, s, C₆H₅CH₂—OCO—), 5.25 (1H, d, J=7 Hz, D₂O exchangeable, urethane NH), 6.2 (2H, complex, 2×NHCHCH₂, 7.9 (3H, s, SCH₃), 7.0-8.5 (11H, complex, 5×CH₂, +NH)

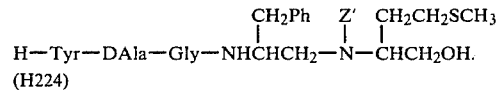

(4) The total product from (3) (0.54 mmol) was dissolved in 80% aqueous trifluoroacetic acid (30 ml) under N₂. After 30 minutes the solvents were evaporated and the residue dried in vacuo. This was dissolved in ethyl acetate and the solution washed twice with 1 M sodium bicarbonate, once with sat. brine, dried over MgSO$_4$ and evaporated to give the free base of the isostere as an oil, 211 mg (98%), t.l.c. (silica) R$_f$ 0.63 n-butanol/acetic acid/H$_2$O (3:1:1).

Approximately one half of this product (94 mg, 0.23 mmol) in DMF (1 ml) was cooled to 0° and added to a preactivated mixture at 0° of Boc-Tyr-DAla-Gly-OH (94 mg, 0.23 mmol), HOBt (70 mg, 0.46 mmol) and DCCI (0.3 mmol in DMF (1.5 ml). The reaction was allowed to warm to room temperature and stirred for two days. After filtration, the mixture was applied to a column (95×2.5 cm) of Sephadex LH20 and eluted with DMF at 15 ml/hour collecting 190 drop (6 ml) fractions. Fractions 35-39 were pooled and evaporated to give 130 mg of product as a colourless glass; t.l.c. (silica) R$_f$ 0.62 chloroform/methanol/acetic acid (85:10:5).

The total amount of fully protected peptide was dissolved in 80% aq. trifluoroacetic acid (25 ml) under N$_2$. After 30 minutes, the solvents were evaporated and the residue dried in vacuo. Most of this product was used in the synthesis of H225 (see below). One fifth of the material was applied to a column (92×1.6 cm) of Sephadex G25 SF in 50% acetic acid run at 10 ml/hr collecting 130 drop (4 ml) fractions. Fractions 24-29 were pooled and chromatographed on a 40×1 cm column of Whatman CM 52 run at 10 ml/hour collecting 100 drop (6 ml) fractions with a linear gradient over 2 days from 0.01 M NH$_4$OAc pH 7 to 0.2 M NH$_4$OAc pH 7. Fractions 37-40 were pooled and lyophilised; then relyophilised from 0.05 M HCl to give 17 mg of fluffy peptide; t.l.c. (silica) R$_f$ 0.80 EtOAc/n-BuOH/AcOH/H$_2$O (1:1:1:1), R$_f$ 0.85 EtOAc/Pyr/AcOH/H$_2$O (50:20:6:11); electrophoresis (cellulose): pH 6.5, 1000 V, 18 mA, 30 minutes, mobility 3.6; pH 2.1, 1000 V, 12 mA, 30 minutes, mobility 3.2 cm; amino acid analysis (after hydrolysis with 6 N HCl+Phenol, 110°, 18 hours) Tyr 0.95, Gly 1.03, AlA 1.02, peptide content 75%.

EXAMPLE 10 H225

The remaining crude sample of H224 from above and methionine (250 mg) were treated with anhydrous liquid HF (10 ml) in the presence of anisole (1 ml) at 0° for 30 minutes. The solvents were carefully evaporated and the residue dried extensively over KOH in vacuo. The residue was dissolved in deaerated 50% aq. acetic acid (2 ml), filtered, and chromatographed in this system on a column (93×2.3 cm) of Sephadex G25 SF run at 12 ml/hour collecting 190 drop (6 ml) fractions. Fractions 56-59 were pooled and evaporated and the residue lyophilised twice from deaerated 0.05 M HCl to give 45.4 mg of white fluffy compound; t.l.c. (silica) R$_f$ 0.66 Et OAc/n-BuOH/AcOH/H$_2$O) (1:1:1:1); R$_f$ 0.70 EtOAc/Pyr/AcOH/H$_2$O (50:20:6:11); electrophoresis (cellulose): pH 6.5, 1000 V, 18 mA, 30 minutes, mobility 6.2 cm; pH 2.1, 1000 V, 12 mA, 30 minutes, mobility 5.2 cm; amino acid analysis (after hydrolysis with 6 NCHl+Phenol) Tyr 0.98, Gly 1.01, Ala 1.01, Peptide content 80%.

EXAMPLE 11 H226

The free base of the isostere (4) from the preparation of H-224 (117 mg, 0.29 mmol) in DMF (1 ml) at 0° was added to a mixture of Boc-Tyr-Gly-Gly-OH (120 mg, 0.29 mmol) and HOBt (88 mg, 0.58 mmol) in DMF (1 ml) at 0° to which two minutes earlier had been added DCCI (0.4 mmol). After two days the reaction mixture was filtered and applied directly to Sephadex LH20 in DMF eluted at 12 ml/hr collecting 190 drop (6 ml) fractions. Fractions 36-39 gave 181 mg of a colourless glass; t.l.c. (silica) R$_f$ 0.58 in chloroform/methanol/acetic acid (85:10:5).

The total product was dissolved in 80% TFA (25 ml) under N$_2$. After 30 minutes the solvent was evaporated and the residue dried. One half of the product was applied to a 93×2.5 cm column of Sephadex G25 SF in 50% acetic acid eluted at 15 ml/hr collecting 190 drop (6 ml) fractions. Fractions 51-55 were pooled, evaporated and lyophilised twice from 0.1 M HCl to give 56.7 mg of white fluffy peptide; t.l.c. (silica) R$_f$ 0.87 EtOAc/n-BuOH/AcOH/H$_2$O (1:1:1:1); R$_f$ 0.75 EtOAc/Pyr/AcOH/H$_2$O (60:20:6:11); electrophoresis (cellulose): pH 6.5, 1000 V, 18 mA, mobility 3.0 cm; pH 2.1, 1000 V, 12 mA, mobility 3.1 cm. Amino acid analysis (after hydrolysis in 6 NCHl+Phenol at 110°, 18 hours) Tyr 0.98, Gly 2.01 (Peptide content 92%).

EXAMPLE 12 H227

The remaining crude sample of H226 was deprotected at 0° for 30 minutes with liquid HF (10 ml) in the presence of methionine (250 mg) and anisole (1 ml). The peptide was isolated as described for H225; from Sephadex G25 SF chromatography, fractions 50-56 gave 48 mg of white fluffy peptide; t.l.c. (silica) R$_f$ 0.72 EtOAc/n-BuOH/AcOH/H$_2$O (1:1:1:1); R$_f$ 0.31 EtOAc/Pyr/AcOH/H$_2$O (60:20:6:11); electrophoresis (cellulose) pH 6.5, 1000 V, 18 mA, 30 minutes, mobility 6.1 cm; pH 2.1, 1000 V, 12 mA, 30 minutes, mobility 5.2 cm; amino acid analysis (after hydrolysis with 6 NHCl+Phenol, 110°, 18 hours) Tyr 1.02 Gly 1.98. Peptide content 84%.

EXAMPLE 13 H229

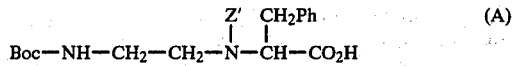

$$\text{Boc—NH—CH}_2\text{—CH}_2\text{—N—CH—CO}_2\text{H} \qquad \text{(A)}$$
with Z′ and CH$_2$Ph substituents on the N and CH.

(1) Boc-NH(CH$_2$)$_2$Br [1.62 g, 7.25 mmol; prep. in 66% yield by reaction of Boc-azide (1.6 g, 11.2 mmol) and 2-bromoethylamine hydrochloride (3.07 g, 15 mmol) in DMF (150 ml) in the presence of NEt$_3$ (3.6 ml, 26 mmol)], phenylalanine ethyl ester hydrochloride (3.36 g, 14.5 mmol) and triethylamine (3.0 ml, 21.75 mmol) in dry DMSO (12 ml) were stirred vigorously at r.t. for 9 days. The mixture was partitioned between ethyl acetate and water, and the organic layer washed with 1 M NaHCO$_3$ (6×). The ethyl acetate layer was dried and evaporated, the residue dissolved in methanol and chromatographed on a column of Sephadex LH20 (90×2.5 cm), eluted with methanol at 10 ml/hr collecting 5 ml fractions. Fractions 88-92 were combined to give the substitution product, 0.30 g as a colourless oil; t.l.c. (silica) R$_f$ 0.58 n-butanol/acetic acid/H$_2$O (3:1:1). Nmr: τ(CDCl$_3$) 2.7 (5H multiplet, ArH), 5.0 (1H, broad, D$_2$O exchangeable, —O—CO—NH—), 4.9 (2H, quartet, J=Hz—OCH$_2$—CH$_3$), 6.7-7.5 (7H, complex, 3×CH$_2$+CH), 8.35 (1H, multiplet, D$_2$O exchangeable, —CH$_2$NH—), 8.6 (9H, s, tBu), 8.9 (3H, triplet, J=7 Hz, CH$_2$CH$_3$).

(2) The reduced isostere from (1) above was reacted overnight with benzyl chloroformate (0.19 ml) in dioxan (5 ml) and 1 M KHCO$_3$ solution (5 ml). Unsym. dimethylethylenediamine (0.1 ml) was added and after 1 day the reaction mixture partitioned between water (after the pH was adjusted to 3.0 by the addition of citric acid) and ethyl acetate. The aqueous phase was extracted twice more with ethyl acetate and the combined organic layers washed with water (2X) and brine, then dried over anhydrous MgSO$_4$ and evaporated to give 0.38 g of a colourless oil; t.l.c. (silica): Rf 0.72 n-butanol/acetic acid/H$_2$O (3:1:1); NMR shows additional peaks to above spectrum: $\tau$(CDCl$_3$) 2.5 (5H, s, ArH), 3.75 (2H, s, —CH$_2$—O—), with loss of 8.35 peak.

(3) The ester from (2) above was dissolved in methanol (5 ml) and 0.2 M NaOH (5 ml) added slowly to the stirred solution. After 18 hours, water (20 ml) was added and the solution extracted with ethyl acetate (2×10 ml). The aqueous phase was acidified to pH 3.0 with citric acid and extracted with ethyl acetate (3×10 ml). The combined organic layers were washed with water (2×10 ml), brine (1×10 ml), and dried over MgSO$_4$. Evaporation gave the product (A) (0.25 g) as a colourless gum; t.l.c. (silica) R$_f$ 0.47 n-butanol/acetic acid/H$_2$O (3:1:1); Nmr: $\tau$(CDCl$_3$) 0.0 (1H, s, D$_2$O exchangeable, —CO$_2$H), 2.5 (5H, s, ArH), 2.7 (5H, multiplet, ArH), 4.7–4.8 (3H, complex, 1H D$_2$O exchangeable PhCH$_2$—O—+NH) 5.85 (1H, broad, CH), 6.5–7.2 (6H, complex, 3×CH$_2$), 8.5 (9H, s, tBu).

(B) Boc-Methionine was coupled to phenolic resin (0.5 g) as usual. After standard acetylation, TFA deprotection and base wash cycles; (A) from above (145 mg, 0.3 mmol) in 1:1 DMF/CH$_2$Cl$_2$ (6 ml) was activated with DCCI (0.45 mmol) and HOBt (92 mg, 0.6 mmol) and added to the resin. After 4½ hours, the resin was thoroughly washed, the base wash cycle repeated and the resin treated with acetyl imidazole overnight. After thorough washing, the resin was dried (0.9 g; >100% increase in weight, still containing DCU).

One half of the resin (0.45 g, ≃0.15 mmol) was replaced in the synthesis vessel, and deprotected with 33% TFA in CH$_2$Cl$_2$ containing 2% diethyl phosphite and 2% ethane dithiol (1 minute and 30 minutes). After base wash, Boc-DAla-OH (0.115 g, 0.6 mmol) was coupled in 1:1 DMF/CH$_2$Cl$_2$ (4 ml) in the presence of HOBt (0.16 g, 1.2 mmol) with DCCI (0.9 mmol). After 2½ hours, the resin was thoroughly washed; TFA and base wash cycles were repeated, and Boc-Tyr-OH (0.17 g, 0.6 mmol) was coupled as previously. After thorough washing, the resin was suspended in 1:1 DMF/MeOH (30 ml) and saturated with anhydrous ammonia. The flask was tightly stoppered and the suspension stirred gently for 2 days. The resin beads were filtered and washed thoroughly with DMF. The combined filtrates were evaporated and chromatographed on Sephadex LH 20 (92×2.5 cms) in DMF at 18 ml/hour collecting 190 drop (6 ml) fractions. Fractions 35–39 were pooled and evaporated to give 110 mg of a glassy residue; t.l.c. (silica) showed a main component in CHCl$_3$/MeOH/AcOH (85:10:5) with R$_f$ 0.53; and a minor component with R$_f$ 0.70. The total product was dissolved in 80% aqueous TFA (25 ml) under N$_2$. After 30 minutes the solvents were evaporated and the residue dried in vacuo over NaOH pellets. This was dissolved in methanol (5 ml) and a sample (1 ml) removed, evaporated and used in the preparation of H228. The remaining material was thoroughly dried, then treated for 30 minutes at 0° with anhydrous liquid hydrogen fluoride (10 ml) in the presence of methionine (250 mg) and anisole (1 ml). The solvents were evaporated and the residue carefully dried, then chromatographed on Sephadex G25 SF (92×2.5 cm) in 50% acetic acid at 18 ml/hr collecting 190 drop (6 ml) fractions. Fractions 53–57 were pooled and evaporated to give the hydrantoin derivative (50.0 mg) as a colourless glass; this was lyophilised several times from 0.05 M HCl to give a white fluffy powder; t.l.c. (silica) R$_f$ 0.72 in EtOAc/n-BuOH/AcOH/H$_2$O (1:1:1:1); R$_f$ 0.78 in EtOAc/Pyr/AcOH/H$_2$O (50:20:6:11); electrophoresis (cellulose) pH 6.5, 1000 V, 18 mA, 30 minutes, mobility 4.0 cm; pH 2.1, 1000 V, 12 mA, 30 minutes, mobility 3.3 cm; Amino acid analysis Tyr 1.00, Ala 1.00; Met 0.22.

EXAMPLE 14 H228

The sample of peptide removed from the preparation of H-229 (see above) was dissolved in 50% deaerated acetic acid and applied to a 93×1.6 cm column of Sephadex G25 SF and eluted at 10 ml/hr collecting 130 drop (4 ml) fractions. The desired Z'-protected derivative was not completely separated on this column and so fractions 27–31 containing both products were pooled and evaporated. The residue was dissolved in 0.01 M ammonium acetate (pH 7) and applied to a 35×1.5 cm column of Whatman CM 52 which was eluted at 15 ml/hour with a linear gradient over two days from 0.01 M to 0.5 M NH$_4$OAc (pH 7) collecting 100 drop fractions. Again inadequate resolution was obtained; fractions 41–47 were pooled and lyophilised. The residue was chromatographed on Sephadex G25 SF (2.5×93 cm) in 50% deaerated acetic acid at 15 ml/hr collecting 190 drop (6 ml) fractions. Fractions 49–51 gave 0.6 mg of the desired product, whereas fractions 52–55 gave 9.5 mg of H229; t.l.c. (silica): R$_f$ 0.81 EtOAc/Pyr/AcOH/H$_2$O (60:20:6:11); R$_f$ 0.91 in EtOAc/n-BuOH/AcOH/H$_2$O (1:1:1:1); electrophoresis (cellulose) pH 6.5, 1000 V, 15 mA, 30 minutes, mobility 4.0 cm.

EXAMPLE 15 H230

Preparation similar to H229. Boc-glycine (0.11 g 0.6 mmol) was coupled to remaining half of isostere-Met resin. After completion of the synthesis, the peptide resin was transamidated and the product chromatographed on Sephadex LH20 in DMF as before: fractions 36–39 gave 118 mg; t.l.c. in chloroform/methanol/acetic acid (85:10:5) R$_f$ 0.45 (single spot). The total peptide was dissolved in 80% TFA (25 ml) under nitrogen. After ten minutes a sample (5 ml) was removed and evaporated; after 3 hours the remaining solution was evaporated. T.l.c. showed the two samples to be identical. The main batch was chromatographed on a 94×2.5 cm column of Sephadex G25 SF in 50% acetic acid and eluted at 18 ml/hr collecting 190 drop (6 ml) fractions. Fractions 64–69 were pooled, evaporated and the residue dried. This was treated with liquid HF as before, again with no change, and was chromatographed on Sephadex G25 SF (93×2.5 cm column) in 50% acetic acid. Fractions 54–58 were pooled, evaporated and repeatedly lyophilised from 0.05 M HCl to give 48 mg of white solid; t.l.c. (silica) R$_f$ 0.61 in ethyl acetate/n-butanol/acetic acid/water (1:1:1:1); R$_f$ 0.50 in ethyl acetate/pyridine/acetic acid/water (60:70:6:11); electrophoresis (cellulose) pH 6.5, 1000 V, 15 mA, 30 minutes, mobility 4.0 cm; pH 2.1, 1000 V, 12 mA, 30 minutes, mobility 3.3 cm. Amino acid analysis: Tyr 0.99, Gly 1.01, Met 0.05.

EXAMPLE 16 H232

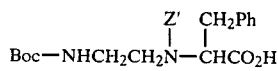

(46 mg, 0.13 mmol), L-methioninol (27 mg, 0.2 mmol) and HOBt (40 mg, 0.26 mmol) were dissolved in DMF (1 ml) and the stirred solution cooled to 0°. A solution of DCCI in methylene chloride (0.1 ml, 0.19 mmol) was added and the reaction stirred for one day, gradually warming to room temperature. The solution was filtered and the filtrate applied directly to a 92×2.5 cm column of Sephadex LH 20, and eluted with DMF at 12 ml/hr collecting 190 drop (6 ml) fractions. Fractions 40-43 were pooled, evaporated, and the residue dried to give 48.2 mg of a colourless glass; $R_f$ (silica) 0.40 in benzene/dioxan/acetic acid (95:25:4); Nmr: $\tau$ (CDCl$_3$) 2.6 (5H, s, ArH), 2.8 (5H, multiplet, ArH) (3H, complex, 1H D$_2$O exchangeable, ArC-H$_2$—O—CO—+NH), 5.8 (1H, t, $\alpha$ —CH), 6.4-8.3 (12H, complex, 6X—CH$_2$—), 8.0 (3H, s, —CH$_3$); 8.6 (9H, s, tBu).

The total product (47 mg, 0.084 mmol) was dissolved in 80% TFA (20 ml) under N$_2$. After 30 minutes the solvents were evaporated and the residue partitioned between ethyl acetate and 1 M sodium bicarbonaate. The organic layer was separated and washed with 1 M sodium bicarbonate and saturated brine; each aqueous wash was back-extracted with ethyl acetate. The combined organic layers were dried and evaporated to give 35.4 mg of an oily residue. This was dissolved in DMF (1 ml) and Boc-Tyr-DAla-OH (30 mg, 0.11 mmol) and HOBt (33.6 mg, 0.22 mmol) added. The stirred solution was cooled to 0° and treated with DCCI solution (0.16 mmol). The reaction was allowed to slowly warm to room temperature. After two days, the solution was filtered and applied to a column of Sephadex LH 20 in DMF as described previously. Fractions 36-39 were pooled and evaporated to give 59 mg of a glassy residue; Nmr $\tau$ (d$_4$MeOH) 2.7 (5H, s, ArH), 2.9 (5H, broad ArH), $\tau_A$ 3.02 $\tau_B$ 3.25 (4H, A$_2$B$_2$, J=9 Hz, 2×2 ortho ArH), 4.9 (2H, s, ArCH$_2$—O—CO—), 5.7-6.2 (4H, complex, 4x $\alpha$ —CH), 6.4-8.3 (14H, complex, 7x—CH$_2$—), 8.0 (3H, s, S—CH$_3$), 8.6 (9H, s, tBu), 8.95 (3H, d, J=7 Hz, =CH—CH$_3$).

The total product was dissolved in 80% TFA (20 ml) under N$_2$. After 30 minutes, the solvents were evaporated and the residue dried. Approximately 40% of this material was chromatographed on Sephadex G25 SF in 50% acetic acid as before. Fractions 48-53 gave 20.9 mg of the desired Z-protected derivative which was lyophilised several times from 0.1 MHCl to give the hydrochloride as a white solid. The NMR (d$_4$MeOH) spectrum was very similar to that of the protected precursor but lacking the 9H, s, $^t$Bu peak at 8.6; t.l.c. (silica): R$_f$ 0.86 in ethyl acetate/n-butanol/acetic acid/H$_2$O (1:1:1:1); R$_f$0.98 in ethyl acetate/Pyr/acetic acid/H$_2$O (60:20:6:11); electrophoresis (cellulose): pH 6.5, 1000 V, 30 minutes, mobility 5.1 cm; pH 2.1, 18 mA, 1000 V, 30 minutes, mobility 4.5 cm, Amino acid analysis: Tyr 0.98, Ala 1.02.

EXAMPLE 17 H231

The remaining 60% of crude H232 was deprotected as usual with HF at 0°, and chromatography on Sephadex G25 SF gave, after lyophilisation from 0.1 M HCl, 18.6 mg of white solid; NMR (d$_4$MeOH) similar to that of H232 but lacking the $\tau$ 2.7 (5H, s, ArH) and 4.9 (2H, s, ArCH$_2$—O—CO—) peaks; t.l.c. (silica) R$_f$ 0.71 in ethyl acetate/n-butanol/acetic acid/H$_2$O (1:1:1:1); R$_f$ 0.73 in ethyl acetate/pyridine/acetic acid/H$_2$O (60:20:6:11); electrophoresis (cellulose) pH 6.5, 25 mA, 1000 V, 30 minutes, mobility 7.3 cm; pH 2.1, 18 mA, 1000 V, 30 minutes, mobility 7.5 cm; amino acid analysis: Tyr 0.99, Ala 1.01.

ANALOGUE H236 EXAMPLE 18

Structure

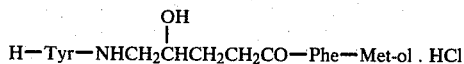

Synthesis (a) Boc-Tyr-NHCH$_2$COCH$_2$CH$_2$CO-Phe-Metol

Boc-Tyrosine was coupled to Cl$^-$N$^+$H$_3$CH$_2$COCH$_2$CH$_2$CO$_2$Me (prepared by esterification of either δ-amino-acid described in scheme 2 or deprotected keto-acid VI in scheme 1) in DMF using DCCI in the presence of 1-hydroxy-benzotriazole (HOBT). After ester hydrolysis a solution of Boc-Tyr-NH-CH$_2$COCH$_2$CH$_2$CO$_2$H (55 mg, 0.12 mmol) in DMF (1.5 ml) was treated at 0° C. with HOBT.H$_2$O (46 mg, 0.30 mmol) and DCCI (0.20 mmol in 0.11 ml DMF). Cl$^-$H$_2$$^+$-Phe-Met-Ol (prepared from Boc-Phe-Met-OMe by sodium borohydride reduction, removal of the N-protecting group using 80% aqueous TFA under N$_2$, and lyophilisation from dilute HCl) (45 mg, 0.14 mmol) was added followed by NEt$_3$ (20 μl, 0.14 mmol). The mixture was stirred at 25° C. for 65 hours and evaporated. The residue was dissolved in EtoAc and washed with KHSO$_4$ solution, H$_2$O, NaHCO$_3$ and brine, dried and evaporated. Trituration with EtoAc afforded Boc-Tyr-NHCH$_2$COCH$_2$CH$_2$-Phe-Met-ol (53 mg):tlc (silica) Rf 0.46 in chloroform/methanol/acetic acid (85:10:5).

(b) Boc-Tyr-NHCH$_2$CH(OH)CH$_2$CH$_2$CO-Phe-Metol, H236

A solution of Boc-Tyr-NHCH$_2$COCH$_2$CH$_2$CO-Phe-Met-ol (30 mg) in MeOH (20 ml) and H$_2$O (7 ml) was treated with sodium borohydride (60 mg). After 1.0 hour at 25° C. the solvents were evaporated and the residue treated with 80% aqueous TFA under N$_2$ for 0.5 hour. Evaporation and chromatography on Sephadex G25-SF in 50% acetic acid gave, after lyophilisation from dilute HCl, H236 (19.0 mg): tlc (silica): Rf 0.50 in n-propanol/water (7:3); Rf 0.60 in ethylacetate/pyridine/acetic acid/water (60:20:6:11). Electrophoretically homogeneous at pH 2.1 and 6.5. Amino-acid analysis: Tyr 0.98, Phe 1.02 (methionine absent).

ANALOGUES H237 AND H238 EXAMPLES 19 AND 20

Structures

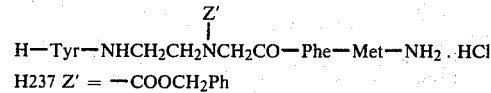

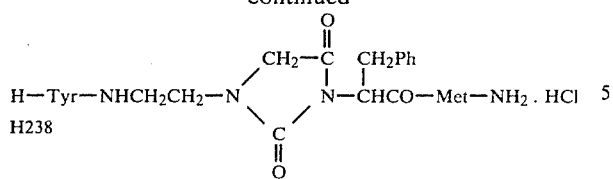
H238

Synthesis

A suspension of Boc-Tyr-NHCH₂CH₂N(Z')CH₂COPheMet-phenyl ester resin (described in the preparation of H218, H219 and H220) (0.20 g) in 1:1 DMF-MeOH (20 ml) was saturated at 0° with dry NH₃ and kept at 25° C. for 2 days. Evaporation, deprotection with 80% aqueous TFA under N₂, followed by chromatography on SP Sephadex C25 (30% acetic acid, 0.01-1.00 M NaCl) and desalting on Sephadex G25 SF in 50% acetic acid gave after lyophilisation from dilute HCl, (i) H237 (23.6 mg); tlc (silica) Rf 0.87 in ethylacetate/pyridine/acetic acid/water (60:20:6:11), Rf 0.78 in ethyl acetate/n-butanol/acetic acid/water (1:1:1:1). Electrophoretically homogeneous at pH 2.1 and 6.5. Amino-acid analysis Tyr 1.00, Phe 1.03, Met 0.97; and (ii) H238 (1.4 mg):tlc (silica) Rf 0.76 in ethyl acetate/pyridine/acetic acid/water (60:20:6:11), Rf 0.76 in ethylacetate/n-butanol/acetic acid/water (1:1:1:1). Electrophoretically homogeneous at pH 2.1 and 6.5. Amino-acid analysis Tyr 1.10, Phe 0.28 (caused by acid stability of hydantoin), Met 0.90.

ANALOGUE H239 EXAMPLE 21

Structure

Synthesis
A suspension of

ester resin (described in the preparation of H229) (0.57 g) in 1:1 DMF-dimethylaminoethanol (30 mls) was stirred gently at 25° C. for 24 hours. The dimethylaminoethyl ester was hydrolysed overnight at pH 9.7 in 1:1 DMF-H₂O. Deprotection with 80% aqueous TFA under N₂ followed by chromatography on Sephadex G25 SF in 50% acetic acid gave, after lyophilisation from dilute HCl, H239 (75.0 mg):tlc (silica) Rf 0.97 in ethyl acetate/pyridine/acetic acid/water (60:20:6:11), Rf 0.77 in ethyl acetate/n-butanol/acetic acid/water (1:1:1:1). Electrophoretically homogeneous at pH 2.1 and 6.5. Amino-acid analysis Tyr 0.99, Ala 1.01, Met. 0.88.

We claim:

1. Compounds of the general formula

R-Tyr-X-Gly-B-Y-Z where (a)

—X is Gly, aza-Gly, aza-Ala or any D-amino acid residue

—B is Phe, N-substituted (particularly N-methyl) -Phe or dehydro-Phe all optionally substituted in the ring, or alternatively cyclohexylalanine —Y is any D- or L-amino acid residue and (b) one or more of the peptide links between Tyr, X, Gly, B and Y is replaced by a group or groups, the same or different, selected from —CH(OH)—CH₂—, —CH(OR)—CH₂—, —CH₂NH—,

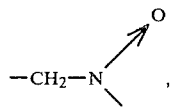

—CH₂—NR—, —CO—CH₂—and (except where X-Gly and the Gly-Gly link is involved) —CH₂CH₂— (where R is an aliphatic or other protective group) and/or any adjacent pair of peptide-bond nitrogen atoms of the backbone is linked to form the structure

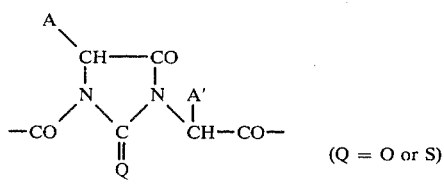
(Q = O or S)

that is to say a carbonyl or thiocarbonyl group links the nitrogen atoms of adjacent amino acid residues, A and A' being the side chains thereof and optionally further with the nitrogen of one or more remaining peptide groups carrying a protective aliphatic or other group as

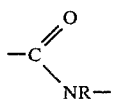

where R is as below and (c)

Z is —NH₂, —NHR, —N(R)₂, —OH or —OR where R is as below and (d)

R is an aliphatic or other protective group.

2. Compounds according to claim 1, where A and A' are selected from the side chains of glycine, alanine, valine, leucine, isoleucine, phenylalanine, tyrosine, proline, hydroxyproline, serine, threonine, cysteine, cystine, methionine, tryptophan, aspartic acid, glutamic acid, arginine, lysine and histidine as such or in protected or modified form.

3. Compounds according to claim 1, wherein A and A' are selected from one of the following combinations
(i) A as the side chain of Gly, aza-Gly, aza-Ala or any D-amino acid residue particularly D-Ala, D-Thr, D-Ser or D-Met, and A' as the side chain of Gly,
(ii) A as the side chain of Gly and A' as the side chain of Phe, N-substituted (particularly N-methyl)-Phe or dehydro-Phe all optionally substituted in the ring by hydroxy, halo, nitro or other groups, or alternatively cyclohexylalanine
(iii) A as the side chain of Phe, N-substituted (particularly N-methyl) -Phe or dehydro-Phe all optionally substituted in the ring by hydroxy, halo, nitro or other groups, or alternatively cyclohexylalanine, and A' as any D- or L-amino acid residue particularly Leu, Nle, Met or the sulphoxide of Met all as such or in aza form; Pro or Hypro; or homoserine lactone; or formal derivatives of any of these in which the terminal

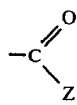

group is replaced by —CH₂—Z (Z is —NH₂, —NHR, —N(R)₂, —OH or —OR where R is an aliphatic or other protective group) or by hydrogen.

4. Compounds according to claim 1, 2 or 3 wherein X is D-Ala, D-Thr, D-Ser or D-Met.

5. Compounds according to claim 1, 2 or 3, wherein ring substituents in B are selected from hydroxy, halogen, nitro or other groups.

6. Compounds according to claim 1, 2 or 3 wherein Y is a D or L amino acid selected from Leu, Nle, Met or the sulphoxide of Met, all as such or in aza form; Pro or Hypro; or homoserine lactone; or formal derivatives of any of these in which the terminal

group is replaced by —CH₂—Z (Z as claim 2) or by hydrogen.

7. Compounds according to claim 1, 2 or 3, wherein R is selected from methyl, ethyl, propyl, cyclopropyl, cyclopropylmethyl, butyl, allyl, phenyl, benzyl or the like or simple halogenated (in particular fluorinated) derivatives thereof; formyl, acetyl or other acyl groups or simple halosubstituted derivatives thereof such as chloroacetyl or trifluoroacetyl; or a substituted derivative such as

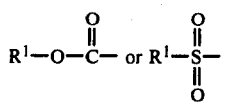

where R¹ may be methyl, ethyl, propyl, cyclopropyl, cyclopropylmethyl, butyl, allyl or the like, or phenyl, or benzyl or ring substituted phenyl or benzyl derivatives, tertiary butyl, or substituted derivatives such as phenylisopropyl, diphenylisopropyl or fluorenylmethylene.

8. The compound

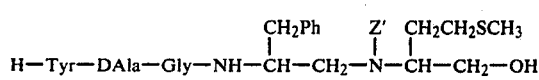

wherein Z' is benzyloxycarbonyl

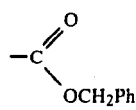

9. The compound:

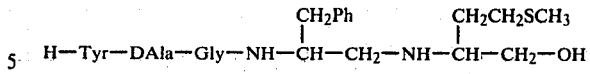

10. The compound:

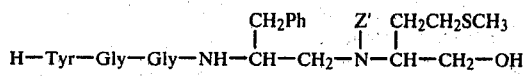

(Z' as claim 8).

11. The compound:

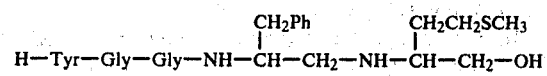

12. The compound:

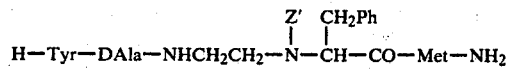

(Z' as claim 8).

13. The compound:

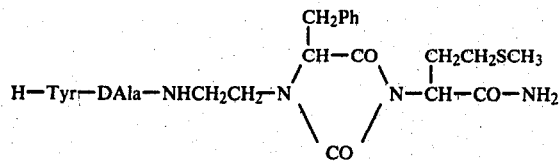

14. The compound:

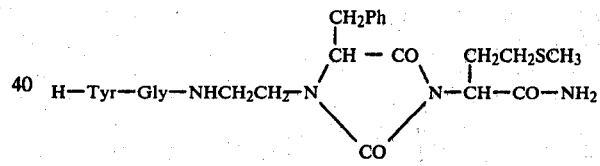

15. The compound:

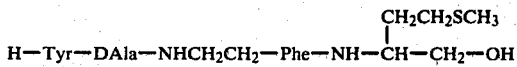

16. The compound:

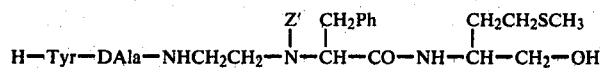

(Z' as claim 8).

17. The compound:

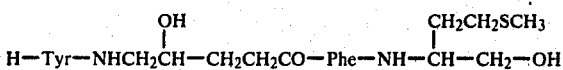

18. The compound:

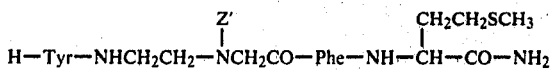

(Z' as claim 8).
19. The compound:
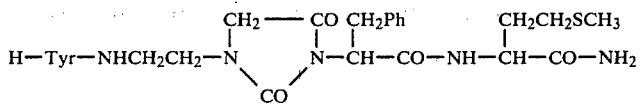
20. The compound:
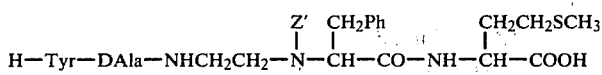
(Z' as claim 8).
21. A compound according to any one of the preceding claims, as such or in pharmaceutically acceptable N-protected or salt form, when made up with a pharmaceutically acceptable diluent or carrier for administration.
* * * * *